United States Patent [19]

Covey et al.

[11] Patent Number: 5,434,274
[45] Date of Patent: Jul. 18, 1995

[54] BENZ(EPSILON)INDENE COMPOUNDS

[75] Inventors: Douglas F. Covey, Ballwin; Yuefei Hu, Clayton; Mingcheng Han; Charles F. Zorumski, both of St. Louis, all of Mo.

[73] Assignee: Washington University, St. Louis, Mo.

[21] Appl. No.: 204,911

[22] Filed: Mar. 2, 1994

Related U.S. Application Data

[60] Continuation-in-part of Ser. No. 4,768, Jan. 14, 1993, Pat. No. 5,292,906, which is a division of Ser. No. 811,208, Dec. 20, 1991, Pat. No. 5,206,415.

[51] Int. Cl.$^6$ ............................................. C07D 317/72
[52] U.S. Cl. ..................................... 549/336; 560/117; 560/256; 558/429; 562/499; 564/459; 568/373; 568/817
[58] Field of Search ..................... 558/429; 549/336; 560/117, 256; 564/459; 568/373, 817; 562/499

[56] References Cited

U.S. PATENT DOCUMENTS

| | | | |
|---|---|---|---|
| 2,830,075 | 4/1958 | Farinacci | 260/168.5 |
| 3,499,913 | 3/1970 | Joly et al. | 260/345.2 |
| 3,676,461 | 7/1972 | Muller et al. | 260/343.3 |
| 3,821,288 | 6/1974 | Crabbe et al. | 260/488 B |
| 3,828,062 | 8/1974 | Furst et al. | 260/307 H |
| 4,874,891 | 10/1989 | Covey et al. | 560/256 |
| 5,206,415 | 4/1993 | Covey et al. | 560/117 |
| 5,292,906 | 3/1994 | Covey et al. | 552/619 |

FOREIGN PATENT DOCUMENTS 301907  2/1989  European Pat. Off. ... C07C 49/617

OTHER PUBLICATIONS

Rodgers–Neame et al., Molec. Pharmacol. 42, 952–957 (1992).
Covey et al., J. Med. Chem. 36, 627–630 (1993).
Hu et al., J. Med. Chem. 36, 3956–3967 (1993).
Morales–Alanis et al., J. Med. Chem. 28, 1796–1803 (1985).
Zomer and Wynberg, Steroids 44, 283–292 (1985).

*Primary Examiner*—Paul J. Killos
*Attorney, Agent, or Firm*—Scott J. Meyer

[57] ABSTRACT

Neuroactive benz[e]indene compounds

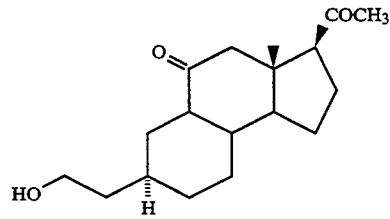

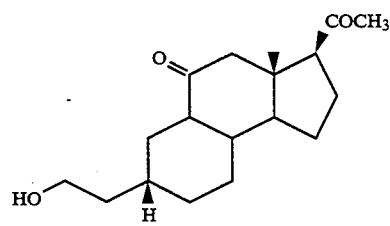

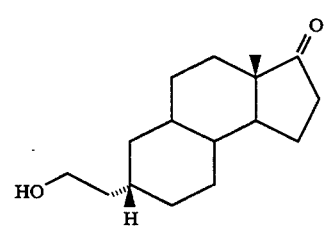

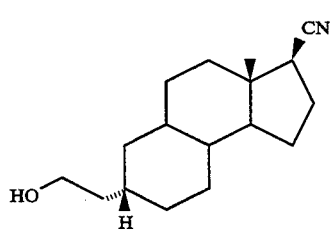

(Abstract continued on next page.)

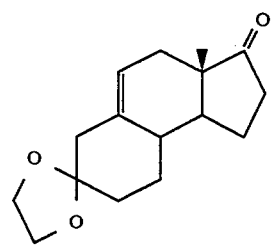
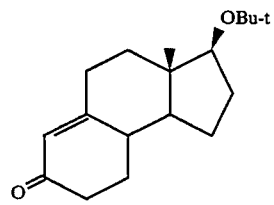
-continued
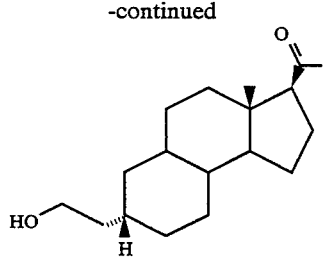
are prepared by a total synthesis from the following three starting materials
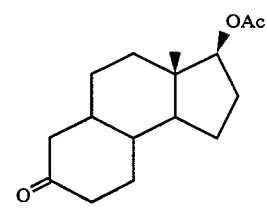
10 Claims, No Drawings

BENZ(EPSILON)INDENE COMPOUNDS

ACKNOWLEDGMENT OF SUPPORT

The invention herein was made in part with government support under NIH grants HD19746, NS14834 and GM47969 and in part with support from Monsanto Company. The government has certain rights in the invention.

CROSS-REFERENCE TO RELATED APPLICATIONS

This is a continuation-in-part of application Ser. No. 08/004,768, filed Jan. 14, 1993, now U.S. Pat. No. 5,292,906, which in turn is a division of application Ser. No. 07/811,208, filed Dec. 20, 1991, now U.S. Pat. No. 5,206,415. The disclosure of said patent is incorporated herein by reference.

BACKGROUND OF THE INVENTION

The present invention relates to benz[e]indene compounds and, more particularly, to a novel method for the total synthesis of these compounds and novel intermediates that are useful in said synthesis. According to U.S. Pat. No. 5,206,415, various neuroactive benz[e]indene compounds and intermediates are prepared by the partial degradation of steroid [tetracyclic] precursors. These benz[e]indene compounds can be envisioned as steroids without an A-ring and, thus, are also referred to as tricyclic steroid analogs. These neuroactive compounds are particularly useful for enhancing gamma-aminobutyric acid (GABA)-induced chloride currents at the GABA receptor/chloride ionophore complex. See Rodgers-Neame et al., *Molec. Pharmacol.* 42, 952–957 (1992); Covey et al., *J. Med. Chem.* 36, 627–630 (1993); and Hu et al., Ibid. 36, 3956–3967 (1993). As distinguished from preparation of these benz[e]indene compounds by partial degradation of steroid precursors, a method for the total synthesis of these compounds would have significant advantages in that the reactions could be more readily manipulated to synthesize preferred compounds.

BRIEF DESCRIPTION OF THE INVENTION

In accordance with the present invention a novel method is provided for the total synthesis of neuroactive benz[e]indene compounds and novel intermediates. The neuroactive compounds are of the type disclosed in U.S. Pat. No. 5,206,415, and can be conveniently represented by the following structural Formulas I and II:

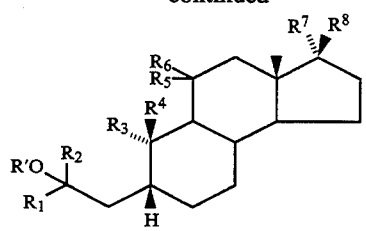 (I)

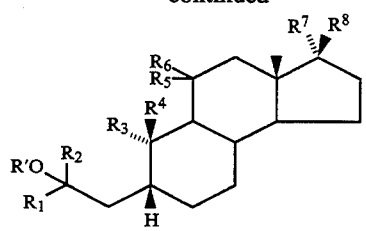 (II)

wherein
$R_1$ = H or $C_1$–$C_4$ alkyl or fluoroalkyl;
$R_2$ = H or $C_1$–$C_4$ alkyl or fluoroalkyl, in which $R_1$ and $R_2$ can be the same or different;
$R_3$ = H or $CH_3$;
$R_4$ = H or $CH_3$, in which $R_3$ and $R_4$ can be the same or different;
$R_5$ = H;
$R_6$ = H;
$R_5, R_6$ = =O(carbonyl);
$R_7$ = H;
$R_8$ = a hydrogen bond accepting group.
$R_7, R_8$ = =O(carbonyl); and
$R'$ = an ester group.

In the above Formulas I and II, the preferred hydrogen bond accepting groups are as follows:

1) ketones (—CO—R″, where R″ can be alkyl or fluoroalkyl groups $C_1$ to $C_4$ or cycloalkyl groups $C_3$ to $C_6$).

2) an α-hydroxy ketone (—CO—CH$_2$OH) or esters thereof (—CO—CH$_2$OXOR‴, where X=C, P=O(OR‴), or S=O; where R‴ can be alkyl groups $C_1$ to $C_{20}$).

3) alkyl esters of carboxylic acids (—COOR‴, —CH$_2$COOR‴, where R‴ can be alkyl groups $C_1$ to $C_{20}$).

4) amines (NHR″ and N(R″)$_2$ where R″ can be alkyl or fluoroalkyl groups $C_1$ to $C_4$ or cycloalkyl groups $C_3$ to $C_6$).

5) a nitrile (CN)

6) a γ-lactone

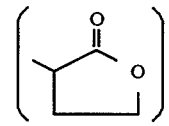

The ester group (R′) can be any group derived from reaction between the hydroxyl group with a $C_1$–$C_{18}$ organic acid, acid halide, anhydride, or ester, such as, e.g., acetic, propionic, n- and i-butyric, n-, i-, s-, and t-valeric, hexanoic, heptanoic, octanoic, nonanoic, decanoic, undecanoic, dodecanoic, palmitic, stearic, cinnamic, benzylic, benzoic, maleic, fumaric, ascorbic, succinic, oxalic, tartaric, citric, fluconic, itaconic, aspartic, and the like.

For convenience of presentation, the numbering system and nomenclature rules associated with steroids in used in the foregoing structural Formulas I and II which are in the 5α- and 5β-configurations (or 7 α- and 7β-configurations according to the benz[e]indene numbering system), respectively.

The total synthesis of the neuroactive benz[e]indene compounds and intermediates in accordance with the present invention employs three known benz[e]indene compounds as starting materials as follows:

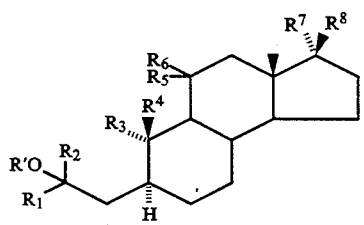

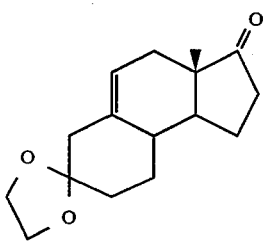

Compound A

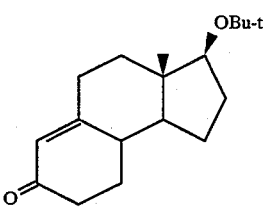

Compound B

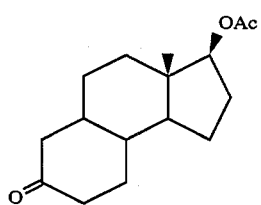

Compound C

Compound A is described by Morales-Alanis et al., *J. Med. Chem.* 28, 1796–1803 (1985). Compound B is described by Zomer and Wynberg, *Steroids* 44, 283–292 (1985). Compound C is described by Takeda and Horibe, Eur. Pat. Appln. EP 301,907, Feb. 1, 1989.

The following preferred neuroactive benz[e]indene compounds of Formulas I and II as described in U.S. Pat. No. 5,206,415, are prepared by total synthesis from these known starting compounds:

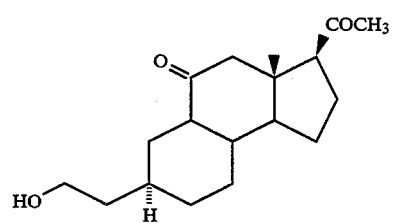

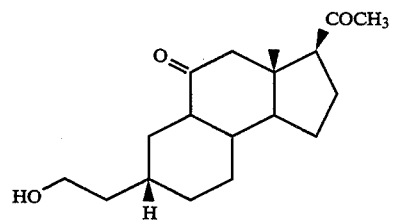

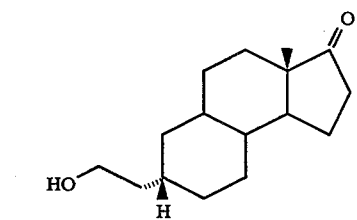

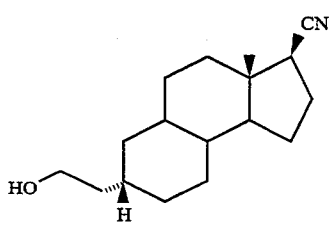

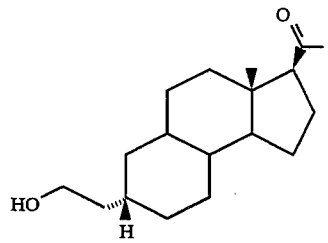

Other tricyclic precursors that can be used as starting materials for the total synthesis of the neuroactive benz[e]indene compounds are described in German Offen. 2,123,027, Dec. 2, 1971.

The total synthesis of preferred compounds of Formulas I and II is conveniently shown in the following Reaction Schemes 1 through 7.

The synthetic methods comprise a series of steps to manipulate tricyclic compounds into the preferred compounds of the invention. Each of the reactions shown in the Reaction Schemes proceeds in adequate to excellent yields. Whenever more than one transformation is indicated on an arrow between structures, the yield reported is the overall yield for the combined transformations. The compounds shown in the Reaction Schemes have been purified by chromatographic methods. In necessary cases, the compounds have been shown to have the correct elemental composition by combustion analysis and have been characterized by infrared and NMR spectroscopy.

Schemes 1 and 2 demonstrate the synthesis of preferred compounds containing an 11-oxo group (This is the numbering used in steriod nomenclature. Using the benz[e]indene nomenclature, this is a 5-oxo group.) The starting material shown in Scheme 1 is a known compound (Compound A, prepared substantially according to the method described by Morales-Alanis et al., supra). Step (b) of Scheme 1 produces a mixture of diasteromeric products that are separated chromatographically prior to continuation of the synthetic route. Accordingly, the synthetic Scheme continues with the diastereomer having the sterochemistry at the ring fusions of the preferred compounds of the invention. Step (c) of Scheme 1 introduces an ethoxycarbonylmethylene group as a mixture of Z and E double bond isomers. Although it is possible to isolate the E double bond isomer in pure form, in practice the mixture of double bond isomers is used for Step (d) to produce a mixture of 5α- and 5β-analogs (This is the numbering used in steroid nomenclature. Using the benz[e]indene nomenclature, this is the 7-position.) The 5α- and 5β-analogs are separated chromatographically before further synthetic transformations are performed.

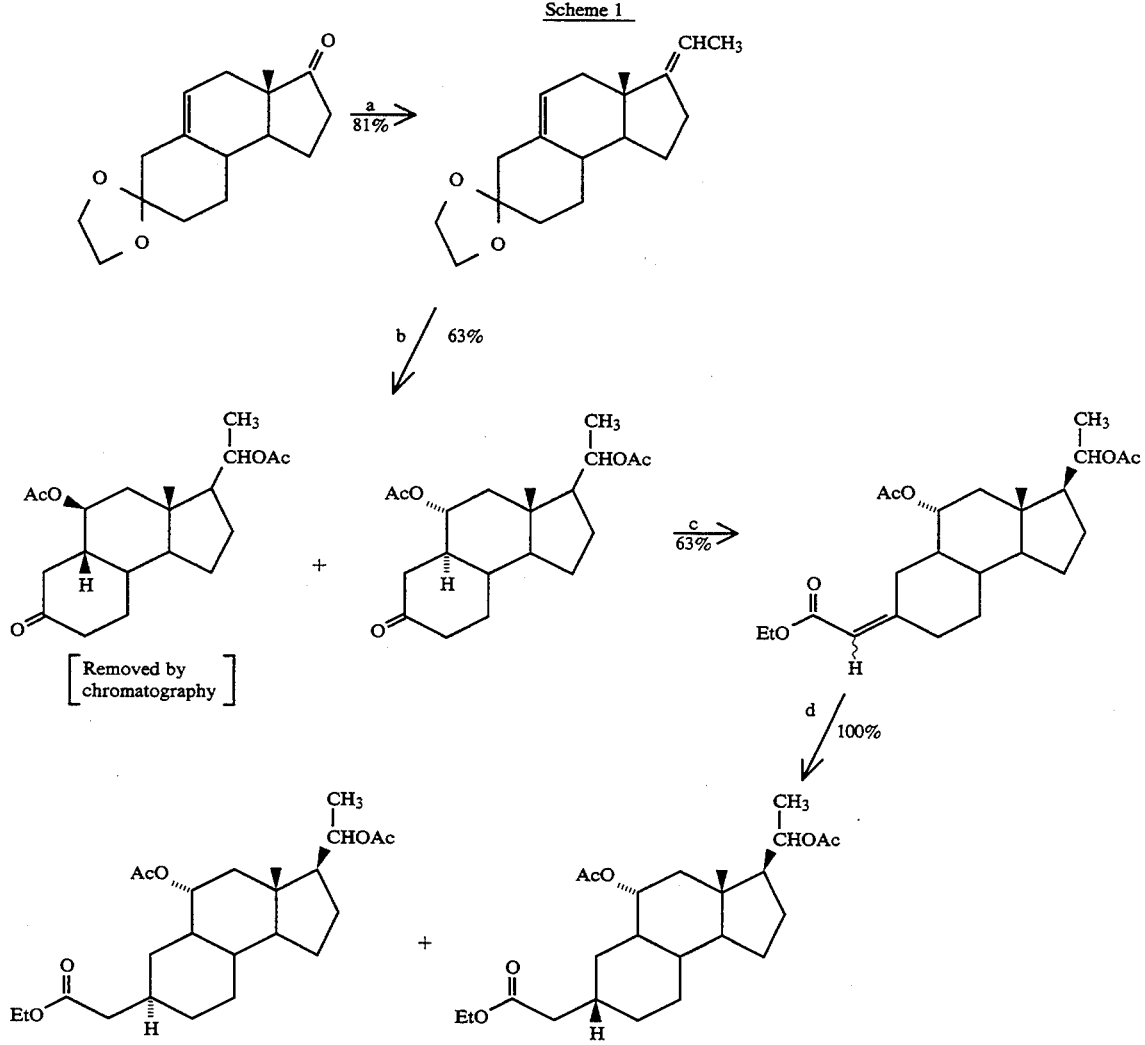

a) (ethyl)triphenylphosphonium bromide, NaH, DMSO;
b) i: BH$_3$—THF, THF; ii: NaOH, H$_2$O$_2$; iii: AcOAc, pyridine;
c) (carbethoxymethylene)triphenylphosphorane;
d) Pd/carbon, H$_2$, EtOAc.

Scheme 2 details the remaining steps needed to prepare either 5α or 5β series of 11-oxo analogs containing the COCH$_3$ hydrogen bond acceptor group of the final compounds. The steps consist of reduction with diisobutylaluminum hydride (DIBALH) to yield a triol [Step (a)]; selective protection of the primary hydroxy group of the triol [Step (b)]; oxidation to convert the unprotected hydroxy groups to oxo groups [Step (c)]; and finally, removal of the protecting group to expose the primary hydroxy group [Step (d)]. During Step (d), some epimerization of the COCH$_3$ group occurs and the epimerized product is removed chromatographically from the preferred compounds of the invention.

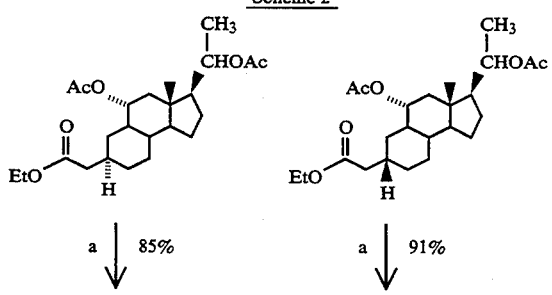

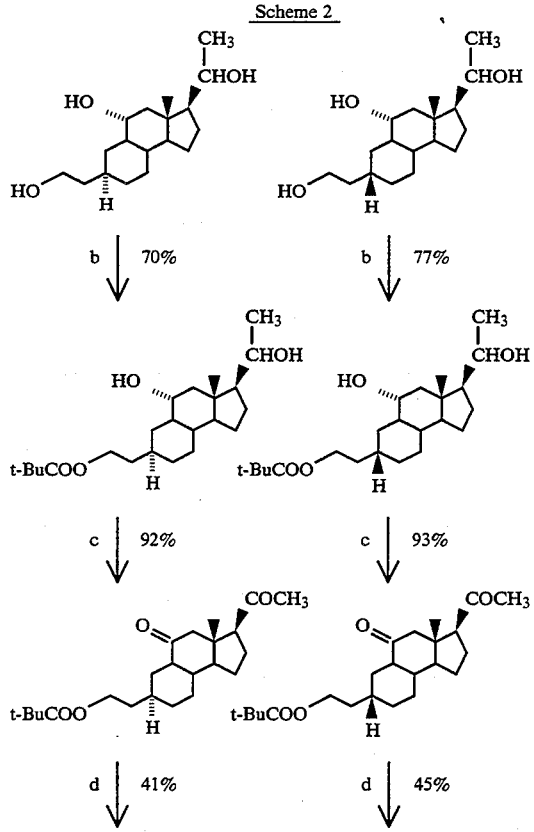

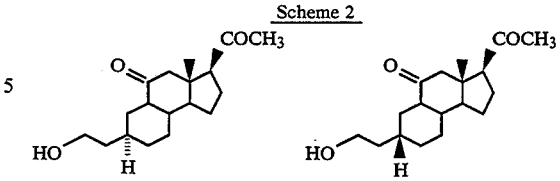

a) DIBALH in toluene;
b) 3-pivaloylthiazolidine-2-thione, NaH, THF;
c) Jones reagent, acetone;
d) KOH, MeOH.

Schemes 3 through 7 summarize the synthesis of preferred compounds without the 11-oxo group. The starting material shown in Scheme 3 is a known compound (Compound B, prepared according to the method described by Zomer and Wynberg, supra.) In Step (a) of Scheme 3 the double bond is removed to give a compound having the stereochemistry at the ring fusions of the preferred compounds of the invention. Step (b) of Scheme 3 introduces an ethoxycarbonyl-methylene group as a mixture of Z and E double bond isomers. Although it is possible to isolate the E and Z double bond isomers in pure form, in practice the mixture of double bond isomers is conveniently used for subsequent transformations. In Step (c) of Scheme 3 the double bond is removed to produce a mixture of 5α- and 5β-analogs whose further transformations are described in Scheme 4. Step (d) of Scheme 3 demonstrates that the ethoxycarbonyl group can be reduced in the presence of the double bond. The double bond can then be subsequently reduced by catalytic hydrogenation to provide an alternate pathway to the 5α- and 5β-analogs shown after Step (d) of Scheme 4.

Scheme 3

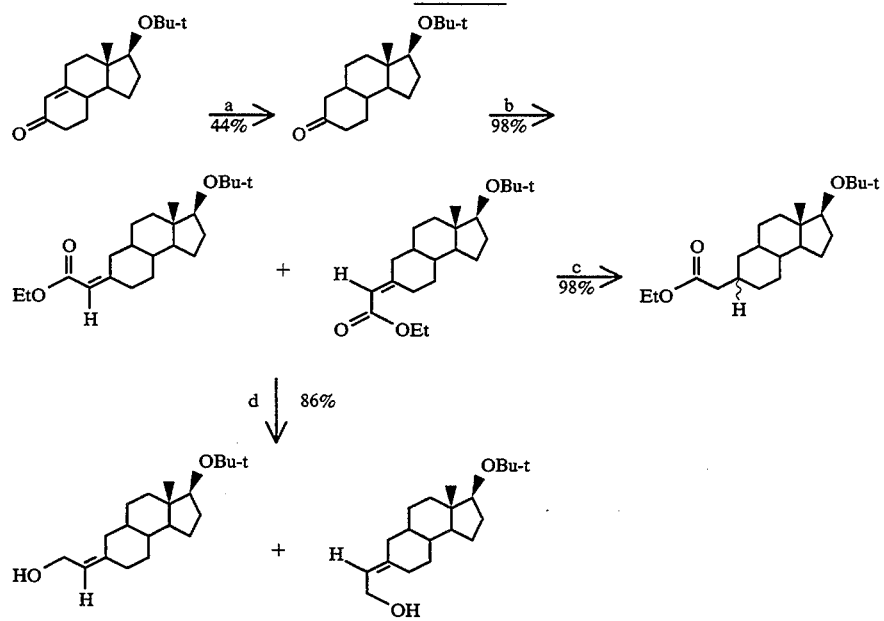

a) Liq. NH₃, Li, THF;
b) (carbethoxymethylene)triphenylphosphorane;
c) Pd/CaCO₃, H₂, N-methylpyrrolidine;
d) DIBALH in toluene, CH₂Cl₂.

Scheme 4 details a novel method for the separation of mixtures of the 5α- and 5β-analogs produced in Step (c)

of Scheme 3. The method consists of reacting these 5α-and 5β-analogs with (S)-(—)-1-)phenylethlamine to yield amide derivatives that can be separated by chromatography [Step (a), Scheme 4]. The separated 5α and 5β series of amides are then converted back to the separated 5α and 5β series of acids [Step (b), Scheme 4], esterified [Step (c), Scheme 4], and reduced to the separated 5α and 5β series of alcohols [Step (d), Scheme 4].

The method is of general utility for the separation of additional 5α- and 5β-analogs [i.e., the separation of various derivatives of (3α, 3aα, 5aβ, 9aα, 9bβ)-benz[e-]indene-7-acetic acids (or esters)]. The method can also work if optically active amines other than (S)-(—)-1-phenylethylamine are used for the preparation of the amide derivatives.

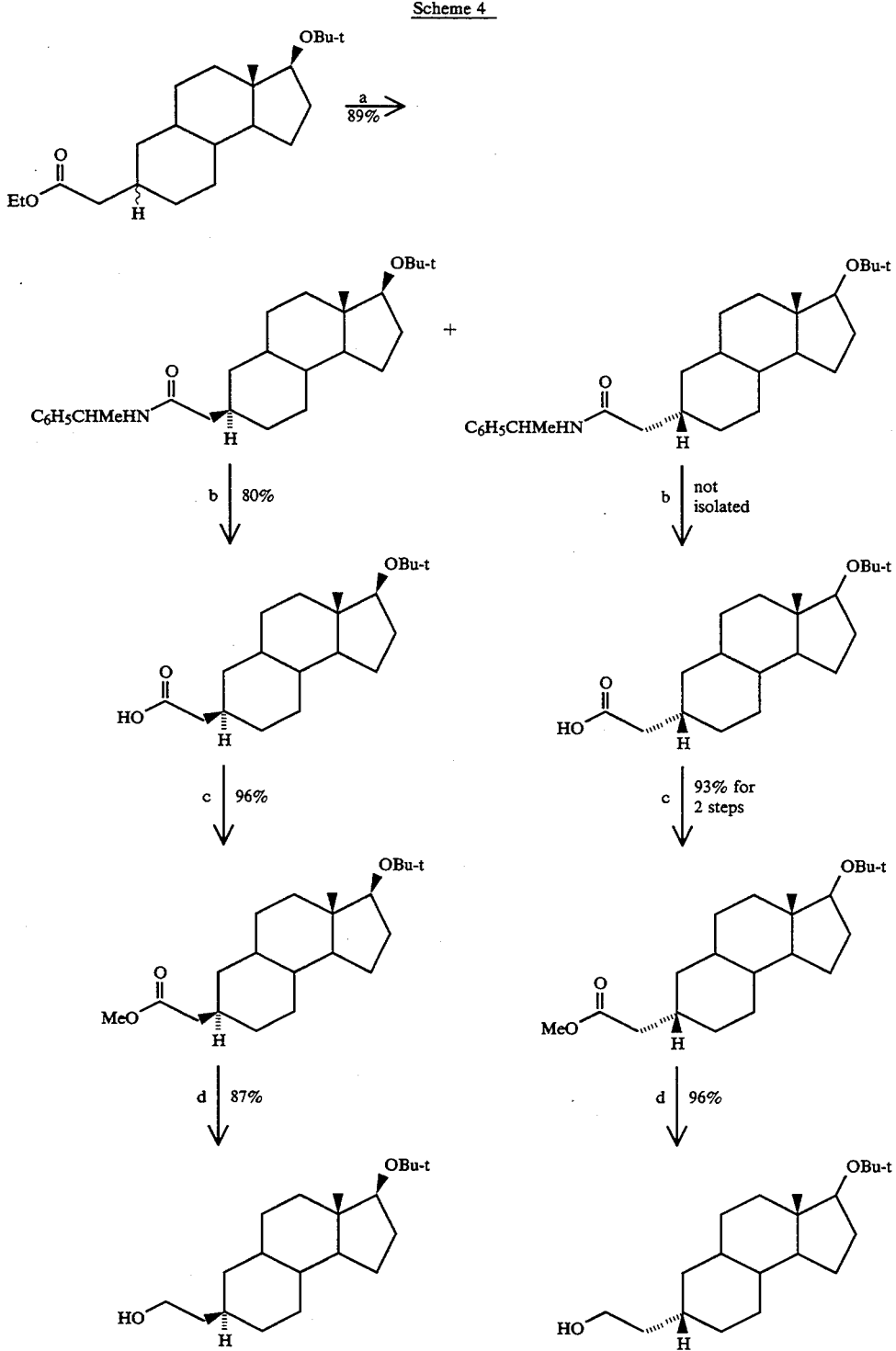

Scheme 4

-continued

Scheme 4 a) i: NaOH, EtOH, H₂O; ii: 1,1'-carbonyldiimidazole, benzene; iii: HOAc, (S)-(−)-α-phenylethylamine;
b) i: HOAc, AcOAc, NaNO₂, ii: dioxane, reflux; iii: NaOH, EtOH, H₂O;
c) diazomethane, ether, EtOH;
d) DIBALH in hexane, CH₂Cl₂.

Scheme 5 demonstrates how the 5β series of alcohols is converted into the preferred compounds of the invention. In Step (a) of Scheme 5, the t-butyloxy group is removed and the resultant diol is selectively oxidized [Step (b), Scheme 5] to give one of the preferred compounds of the invention. In Step (c) of Scheme 5, the oxo group is converted into a cyano group. The cyano compound is obtained as a mixture of two isomers. The isomer which is a preferred compound of the invention is obtained following chromatographic purification. The cyano group of the unseparated cyano compounds can also be transformed into the COCH₃ group [Step (d), Scheme 5]. The isomer containing the COCH₃ which is a preferred compound of the invention is obtained following chromatographic purification.

5α series of preferred compounds of the invention can be prepared by application of the same synthetic steps shown in Scheme 5 to the alternative 5α alcohol shown at the bottom left of Scheme 4. Accordingly, removal of the t-butyloxy group will give a diol in the 5α series, as shown below. The synthesis of this diol in the 5α series of compounds by a degradation route that starts with a steriod precursor has been described in U.S. Pat. No. 5,206,415. The physical properties of the diol are given in Example 9 of U.S. Pat. No. 5,206,415.

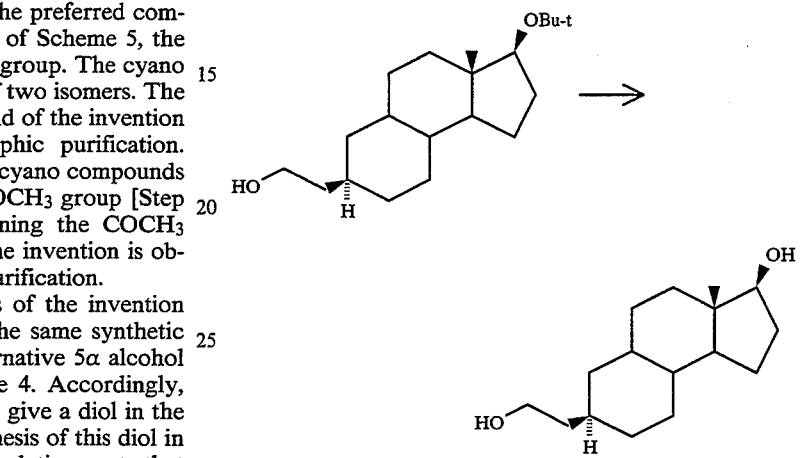

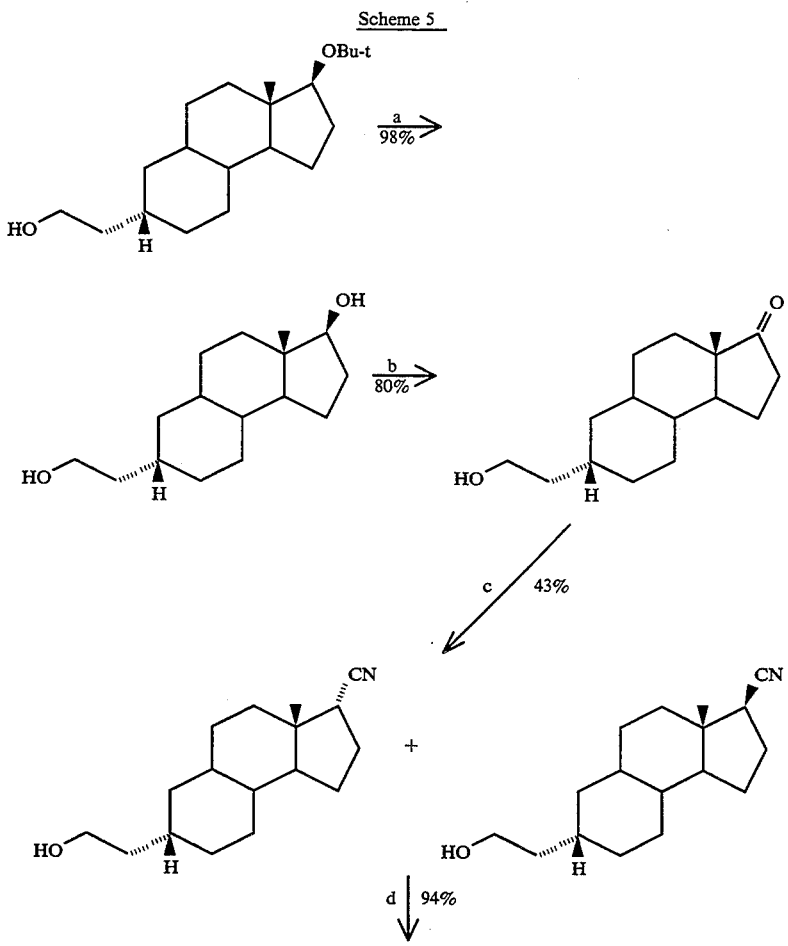

Scheme 5

Scheme 5

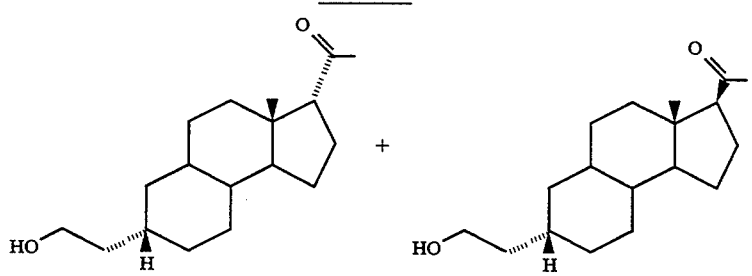

a) HCl, EtOH, H₂O;
b) 5.25% NaOCl, HOAc;
c) i: dimethoxyethane, EtOH, t-BuOK; ii: tosylmethyl isocyanide, dimethoxyethane;
d) CH₃MgCl, THF.

Schemes 6 and 7 describe additional intermediates that are of use for the preparation of the preferred compounds of the invention. The starting material shown in Scheme 6 is a known compound (Compound C, prepared as described by Takeda and Horibe, supra). In Step (a) of Scheme 6, an ethoxycarbonylmethylene group is introduced. A mixture of Z and E double bond isomers is obtained as the product. These double bond isomers were separated by chromatography for chemical characterization or used as a mixture for the subsequent steps shown in Scheme 6. The ethoxycarbonyl group is reduced in the presence of the double bond to give diols [Step (b), Scheme 6]. These diols are not readily separated into Z and E double bond isomers. Consequently, the allylic alcohol groups of the diols were selectively acetylated [Step (c), Scheme 6] to give monoacetate derivatives that could be separated into the Z and E double bond isomers. These separated Z and E double bond isomers were converted back into the separated diols [Step (d), Scheme 6]. A mixture of the isomeric monoacetate derivatives was also oxidized into oxo compounds [Step (e), Scheme 6]. The resultant oxo compounds can either be separated into their Z and E double bond isomers, or used as a mixture [Step (f)] to produce the final compounds of Scheme 6. The double bond can then be subsequently reduced by catalytic hydrogenation to provide an alternate pathway to the oxo compounds in the 5α and 5β series that are preferred compounds of the invention. Scheme 7 demonstrates that the unseparated oxo compounds produced in Step (e) of Scheme 6 can be converted into a mixture of four isomeric cyano compounds. These cyano compounds can be separated by chromatography. The double bond present in the cyano compounds can be reduced, thereby providing an alternate pathway to the cyano compounds in the 5α and 5β series that are preferred compounds of the invention.

Scheme 6

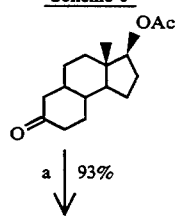

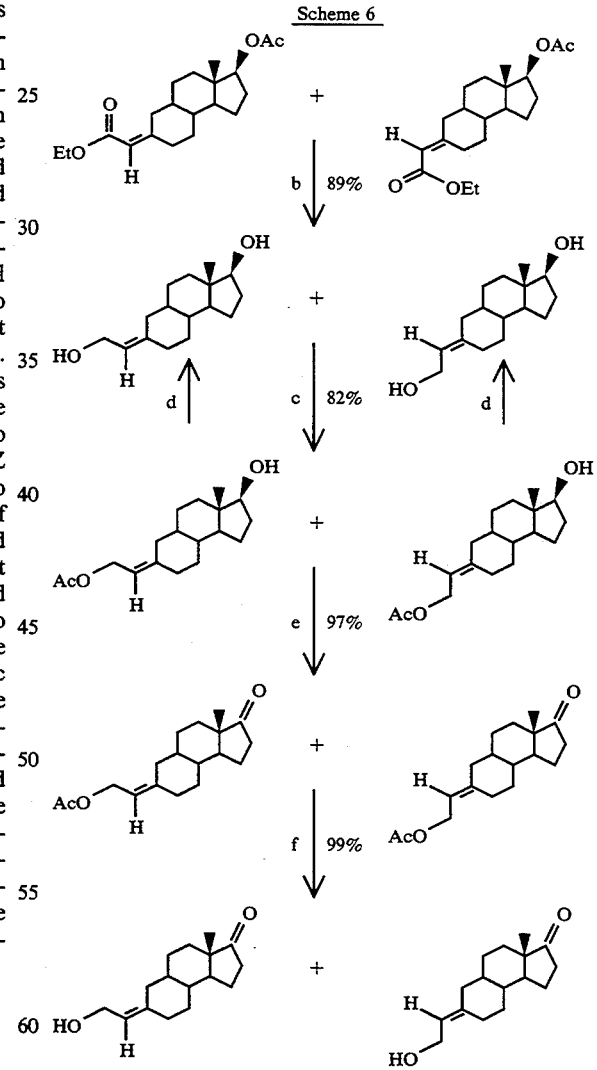

a) (carbethoxymethylene)triphenylphosphorane;
b) DIBALH in hexane, CH₂Cl₂;
c) dry collidene, acetyl chloride;
d) K₂CO₃, MeOH, H₂O;
e) Jones reagent, acetone;
f) K₂CO₃, MeOH, H₂O.

15

Scheme 7

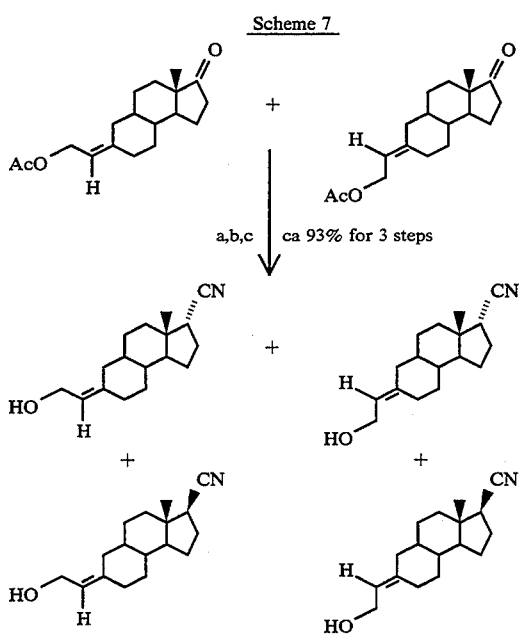

a) diethyl phosphorocyanidate, LiCN, THF;
b) SmI$_2$ in THF, MeOH/THF;
c) K$_2$CO$_3$, MeOH, H$_2$O.

The neuroactive 1-H-benz[e]indene dodecahydro compounds have been biologically evaluated on currents gated by 1 μM GABA, and the responses compared to effects produced by a 3α-OH-DHP, a neurosteroid known to augment GABA responses. These compounds exhibit reversible GABA potentiating effects at 1 μM and three of the preferred four compounds enhance GABA currents to a greater extent than 3α-OH-DHP.

The active compounds are useful for treating disorders which can be ameliorated by increasing neuronal inhibition via modulation of GABA-regulated chloride channels. Thus, the compounds have utility as anxiolytics, anticonvulsants, sedative hypnotics, and agents to treat premenstrual syndrome. The compounds may also be useful as anesthetics. The compounds are formulated according to conventional methods, and may be administered systematically by injection subcutaneously, intravenously, or intraperitoneally, as well as by oral or transdermal administration. The pharmaceutical compositions containing these compounds will, of course, depend on the route of administration.

Parenteral administration is generally characterized by injection, whether subcutaneously, intramuscularly, or intravenously. Injectables can be prepared in conventional forms, either as solutions or suspensions, in solid forms suitable for solution or suspension in liquid prior to injections or as emulsions. Suitable excipients include water, saline, dextrose, glycerol, and the like. If desired, the pharmaceutical compositions may also include minor amounts of nontoxic auxiliary substances, such as wetting or emulsifying agents, pH-buffering agents, and so forth.

For oral administration, the active ingredient is generally administered as a syrup, capsule, or tablet and pharmaceutically nontoxic compositions are formed using the normally employed excipients, such as pharmaceutical grades of mannitol, lactose, starch, magnesium stearate, talcum, cellulose, magnesium carbonate, and so forth. The compositions include sustained release formulations and contain about 10–95% active ingredient with the remainder carrier, as a general rule.

For administration via suppository, conventional binders and carriers include, for example, polyalkylene glycols or triglycerides, and the suppositories generally contain active ingredient in the range of about 0.5–10%. Standard methods of formulating compounds for administration as pharmaceuticals can be found in Remington's Pharmaceutical Sciences, Mack Publishing Company, Easton, Pa., latest edition.

The amount of active compound to be administered depends on the subject being treated, the severity of the condition being treated, the manner of administration, and the judgment of the physician. However, an effective dose is in the range of about 0.5–500 mg/day per typical subject.

DETAILED DESCRIPTION OF THE INVENTION

While the specification concludes with claims particularly pointing out and distinctly claiming the subject matter regarded as forming the invention, it is believed that the invention will be better understood from the following detailed illustrative examples. It will be appreciated, however, that the invention is not limited to these specific detailed examples which are provided for purposes of illustration and not limitation.

In these specific examples, the three known starting materials described hereinbefore, namely Compounds A, B and C, are used as follows: Compound A is used as a starting material in Example 1; Compound B is used as a starting material in Example 13; and Compound C is used as a starting material in Example 27. The Reaction Schemes 1 through 7 described hereinbefore are illustrated in detail in these specific examples as follows: Reaction Scheme 1 is illustrated by Examples 1–4; Reaction Scheme 2 is illustrated by Examples 4–12; Reaction Scheme 3 is illustrated by Examples 13–16; Reaction Scheme 4 is illustrated by Examples 15 and 17–22; Reaction Scheme 5 is illustrated by Examples 22–26; Reaction Scheme 6 is illustrated by Examples 27–31; and Reaction Scheme 7 is illustrated by Examples 31–32. The active preferred compounds of Formulas I and II, above, were synthesized as final products in Examples 8b, 12b, 24, 25b and 26b.

EXAMPLE 1

PREPARATION OF

[3aS-(3E,3aα,9aα,9bβ)]-3-(Ethylidene)-1,2,3,3a,4,6,8,9-,9a,9b-decahydro-3a-methyl-spiro[7H-benz[e]indene-7,2'-[1,3]dioxolane]

A solution of NaH (600 mg, 2.5 mmol) in dry DMSO (20 mL) was warmed to 75°–80° C. for 45 min under nitrogen. The resulting solution was cooled in an ice-water bath and (ethyl)triphenylphosphonium bromide (9.28 g, 25 mmol) in DMSO (30 mL) was added. After 10 min at room temperature, a solution of [3aS-(3aα,-9aα,9bβ)]-1,2,4,6,8,9,9a,9b-Octahydro-3a-methyl-spiro[7H-benz[e]indene-7,2'-[1,3]dioxolan]-3(3aH)-one (1.3 g, 5 mmol) in DMSO (20 mL) was added and the mixture was stirred overnight (22 h) at 60°–70° C. under nitrogen. The mixture then was cooled to room temperature and poured into water (500 mL) and extracted with hexane (5×50 mL). The organic layer was evaporated to give an oil, which was purified by chromatography (silica gel, 30% EtOAc in hexane) to give 1.1 g (81%) of product as a colorless oil.

IR (film, NaCl): 2941, 2871, 1437, 1369, 1106 cm$^{-1}$. $^1$H NMR (CDCl$_3$): δ5.38–5.31 (m, 1H, =CH), 5.22–5.17 (m, 1H, =CH), 3.97–3.92 (m, 4H, 2×CH$_2$O), 1.64 (d, J=5.5 Hz, 3H, CH$_3$), 0.85 (s, 3H, CH$_3$). $^{13}$C NMR(CDCl$_3$): δ149.52 (=C), 136.32 (=C), 122.04 (=C), 114.38 (=C), 109.15 (O—C—O), 64.39 (CH$_2$O), 64.12 (CH$_2$O), 16.98 (CH$_3$), 14.05 (CH$_3$). Structure:

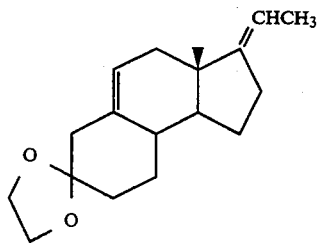

EXAMPLE 2

PREPARATION OF

[3S-[3α(S*),3aα,5β,5aβ,9aα, 9bβ]]-5-(Acetyloxy)-3-[1-(acetyloxy)ethyl]dodecahydro-3a-methyl-7H-benz[e]inden-7-one (2a) and

[3S-[3α(S*),3aα,5α,5aα,9aα,9bβ]]-5-(Acetyloxy)-3-[1-(acetyloxy)ethyl]dodecahydro-3a-methyl-7H-benz[e]inden-7-one (2b)

To a solution of the compound of Example 1 (4.8 g, 17.5 mmol) in dry THF (100 mL) was added a solution of borane-THF complex (1.0M borane in THF, 50 mL, 50 mmol) at room temperature with stirring. After 3 h, the mixture was cooled to 10° C. and aq. 10% NaOH (50 mL) was added cautiously, followed by addition of 30% H$_2$O$_2$ (50 mL) within 20 min. After stirring 2 h at 0° C., the mixture was extracted with EtOAc (3×100 mL) and the combined organic layers were washed with brine (2×50 mL) and dried over Na$_2$SO$_4$. Evaporation of solvent gave the hydroboration product as an oil.

The foregoing crude product was dissolved in THF (25 mL) and 2N aq. HCl (10 mL). The solution was stirred overnight at room temperature under nitrogen. Most of THF was removed under vacuum and the aqueous layer was extracted with EtOAc (3×60 mL) and the combined organic layers were dried over Na$_2$SO$_4$. Evaporation of solvent gave the hydrolysis product as an oil.

The foregoing crude product was dissolved in acetic anhydride (20 mL) and pyridine (10 mL) and the mixture was warmed to 100° C. for 3 h. The excess acetic anhydride and pyridine were evaporated to give an oil which was purified by chromatography (silica gel, 30% EtOAc in hexane) to give a mixture of isomers 2a and 2b in the ratio of ~12:1 as a colorless oil which was separated by HPLC (silica gel, 30% EtOAc in hexane, 3.0 mL/min).

Compound 2a (3.54 g, 58%) was obtained as a colorless oil. IR (film, NaCl): 2958, 2877, 1733, 1432, 1371, 1246 cm$^{-1}$. $^1$H NMR (CDCl$_3$): δ4.97–4.88 (m, 2H, 2×CHOAc), 2.03 (s, 3H, CH$_3$COO), 2.01 (s, 3H, CH$_3$COO), 1.23 (d, J=6.1 Hz, 3H, CH$_3$CHOAc), 0.86 (s, 3H, CH$_3$). $^{13}$C NMR (CDCl$_3$): δ209.69 (CO), 170.26 (COO), 170.07 (COO), 73.42 (CHOAc), 72.06 (CHOAc), 21.07 (CH$_3$COO), 20.86 (CH$_3$COO), 20.26 (CH$_3$CHOAc), 13.28 (CH$_3$). Elemental Analysis: For C$_{20}$H$_{30}$O$_5$. Calcd: C, 68.55; H, 8.62. Found: C, 68.29; H, 8.36. Structure:

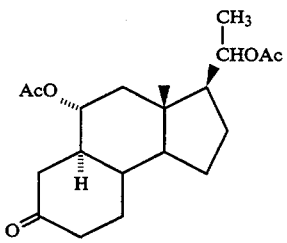

Compound 2b (280 mg, 5%) was obtained as colorless crystals: mp 147°–149° C. IR (film, NaCl): 2957, 2876, 1729, 1432, 1371, 1249 cm$^{-1}$. $^1$H NMR (CDCl$_3$): δ4.87–4.79 (m, 2H, 2×CHOAc), 2.03 (s, 3H, CH$_3$COO), 2.02 (s, 3H, CH$_3$COO), 1.16 (d, J=6.1 Hz, CH$_3$CHOAc), 0.80 (s, 3H, CH$_3$). $^{13}$C NMR (CDCl$_3$): δ210.12 (CO), 170.56 (COO), 170.35 (COO), 74.12 (CHOAc), 72.48 (CHOAc), 21.43 (CH$_3$COO), 21.13 (CH$_3$COO), 19.75 (CH$_3$CHOAc). Elemental Analysis: For C$_{20}$H$_{30}$O$_5$. Calcd: C, 68.55; H, 8.62. Found: C, 68.52; H, 8.64. Structure:

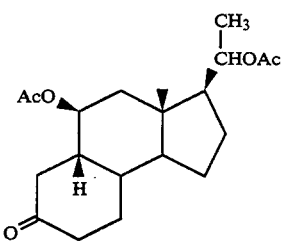

EXAMPLE 3

PREPARATION OF

[3S-[3α(S*),3aα,5β,5aβ,7E,9aα,9bβ]]-3-[1-(Acetyloxy)ethyl]-7-(ethoxycarbonylmethylene)dodecahydro-3a-methyl-1H-benz[e]inden-5-ol acetate (3E) and

[3S-[3α(S*),3aα,5β,5aβ,7Z,9aα,9bβ]]-3-[1-(Acetyloxy)ethyl]-7-(ethoxycarbonylmethylene)dodecahydro-3a-methyl-1H-benz[e]inden-5-ol acetate (3Z)

Compound 2a (140 mg, 0.39 mmol) of Example 2 and (carbethoxymethylene)triphenylphosphorane (280 mg, 0.8 mmol) were heated to 160° C. overnight (ca. 15 h) under nitrogen with stirring. The resultant brown colored liquid was cooled to room temperature and EtOAc (50 mL) was added. The solution was washed with water (50 mL) and brine (50 mL) and dried over Na$_2$SO$_4$. Evaporation of the solvent yielded a gum which was purified by chromatography (silica gel, 15% EtOAc in hexane) to give 110 mg (63%) of the mixture of E- and Z-isomers as an oil. Compound 3E crystallized from the mixture upon cooling in a refrigerator overnight. Compound 3Z could not be separated from the remaining product mixture. In practice, the mixture was used for the next step without separation of products 3E and 3Z.

Compound 3E was obtained as colorless crystals: mp 129°–131° C. (from diethyl ether). IR (film, NaCl): 2953, 2880, 1733, 1650, 1446, 1370, 1246 cm$^{-1}$. $^1$H NMR (CDCl$_3$): δ5.56–5.54 (m, 1H, HC=), 4.94–4.87 (m, 2H, 2×CHOAc), 4.14 (q, J=7.1 Hz, 2H, OCH$_2$CH$_3$), 2.05

(s, 3H, CH$_3$COO), 2.01 (s, 3H, CH$_3$COO), 1.26 (t, J=7.1 Hz, 3H, CH$_3$CH$_2$), 1.22 (d, J=7.1 Hz, 3H, CH$_3$CHOAc), 0.80 (s, 3H, CH$_3$). $^{13}$C NMR (CDCl$_3$): δ171.67 (COOEt), 170.64 (COO), 170.36 (COO), 130.15 (C=), 124.49 (C=), 75.11 (CHOAc), 72.59 (CHOAc), 21.29 (2×CH$_3$COO), 20.52 (CH$_3$CHOAc). Elemental Analysis: For C$_{24}$H$_{36}$O$_6$. Calcd: C, 68.55; H, 8.63. Found: C, 68.70; H, 8.65. Structure:

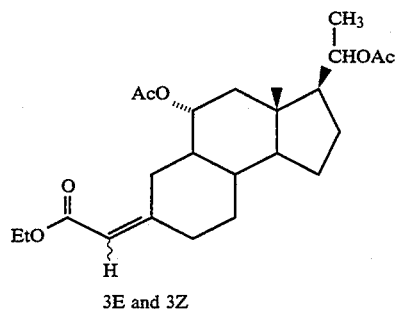

3E and 3Z

EXAMPLE 4

PREPARATION OF

[3S-[3α(S*),3aα,5β,5aβ,7α,9aα,9bβ]]-5-(Acetyloxy)-3-[1-(acetyloxy)ethyl]-dodecahydro-3a-methyl-1H-benz[e]indene-7-acetic acid ethyl ester (4a) and

[3S-[3α(S*),3aα,5β,5aβ,7β,9aα,9bβ]]-5-(Acetyloxy)-3-[1-(acetyloxy)ethyl]-dodecahydro-3a-methyl-1H-benz[e]indene-7-acetic acid ethyl ester (4b)

A solution of compounds 3E and 3Z of Example 3 (200 mg) and Pd catalyst (10% Pd on carbon, 20 mg) in ethyl acetate (20 mL) was stirred in a metal vessel under 550 psi of hydrogen at 65° C. for 20 h. Then the mixture was cooled to room temperature, the solution was filtered, and the solvent was evaporated to yield a crude product which was purified by chromatography (silica gel, 15% EtOAc in hexane) to give a mixture of isomers 4a and 4b (~1:1) as a colorless oil in quantitative yield. Most of compound 4a crystallized from a solution of the isomers dissolved in 5% diethyl ether-hexane upon standing at −20° C. for 20 h. The remaining amount of products 4a and 4b was separated by reverse phase HPLC (C18 column eluted with 65% acetone in water, 3.5 mL/min).

Compound 4a was obtained as colorless crystals: mp 107°-8° C. (from Et$_2$O-hexane). IR (film, NaCl): 2931, 1734, 1446, 1372, 1245 cm$^{-1}$. $^1$H NMR (CDCl$_3$): δ4.93-4.78 (m, 2H, 2×CHOAc), 4.12 (q, J=7.1 Hz, 2H, CH$_2$CH$_3$), 2.03 (s, 3H, CH$_3$COO), 2.00 (s, 3H, CH$_3$COO), 1.20 (t, J=7.1 Hz, 3H, CH$_2$CH$_3$), 1.22 (d, J=6.1 Hz, 3H, CH$_3$CHOAc), 0.77 (s, 3H, CH$_3$). $^{13}$C NMR (CDCl$_3$): δ172.58 (COOEt), 170.47 (COO), 170.15 (COO), 73.86 (CHOAc), 72.45 (CHOAc), 59.88 (OCH$_2$CH$_3$), 21.13 (CH$_3$COO), 21.05 (CH$_3$COO), 20.35 (CH$_3$CHOAc), 14.09 (CH$_3$CH$_2$O), 13.33 (CH$_3$). Elemental Analysis: For C$_{24}$H$_{38}$O$_6$. Calcd: C, 68.22; H, 9.06. Found: C, 68.42; H, 9.12. Structure:

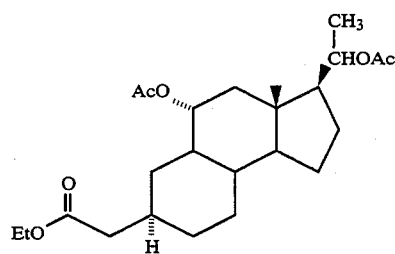

Compound 4b was obtained as colorless crystals: mp 66°-68° C. (from hexane). IR (film, NaCl): 2931, 1734, 1447, 1371, 1246 cm$^{-1}$. $^1$H NMR (CDCl$_3$): δ4.95-4.72 (m, 2H, 2×CHOAc), 4.13 (q, J=7.1 Hz, 2H, CH$_2$CH$_3$), 2.01 (s, 3H, CH$_3$COO), 2.00 (s, 3H, CH$_3$COO), 1.26 (t, J=7.1 Hz, 3H, CH$_2$CH$_3$), 1.21 (d, J=6.2 Hz, 3H, CH$_3$CHOAc), 0.77 (s, 3H, CH$_3$). $^{13}$C NMR (CDCl$_3$): δ172.95 (COOEt), 170.44 (COO), 170.17 (COO), 73.86 (CHOAc), 72.48 (CHOAc), 59.93 (OCH$_2$CH$_3$), 21.13 (CH$_3$COO), 21.01 (CH$_3$COO), 20.34 (CH$_3$CHOAc). Elemental Analysis: For C$_{24}$H$_{38}$O$_6$. Calcd: C, 68.22; H, 9.06. Found: C, 68.44; H, 9.33. Structure:

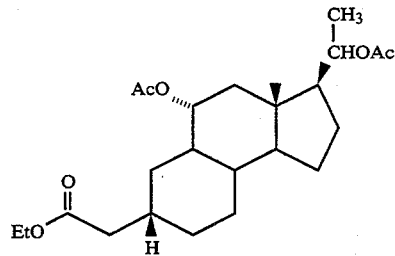

EXAMPLE 5

PREPARATION OF

[3S-[3α(S*),3aα,5β,5aβ,7α,9aα,9bβ]]-Dodecahydro-3-(1-hydroxyethyl)-7-(2-hydroxyethyl)-3a-methyl-1H-benz[e]inden-5-ol To a stirred solution of compound 4a (470 mg, 1.07 mmol) of Example 4 in dry toluene (100 mL) was added a solution of DIBALH in toluene (1.0M solution in toluene, 20 mL, 20 mmol) at −5° C. under nitrogen. After addition of DIBALH, the reaction was allowed to warm and was maintained at room temperature for 1 h. Then the reaction was cooled to 0°-5° C., satd. aq. NH$_4$Cl (50 mL) and 2N HCl (25 mL) were added and stirring was continued until the mixture became clear. The organic layer was separated and the aqueous layer was saturated with NaCl and extracted with THF (2×50 mL) and EtOAc (50 mL). The combined organic layers were dried over Na$_2$SO$_4$. The solvent was removed to give a solid, which was recrystallized from MeOH to give the product (270 mg, 85%) as crystalline white needles: mp 183°-185° C.

IR (film, NaCl): 3307, 2910, 1446, 1039 cm$^{-1}$. $^1$H NMR (CDCl$_3$): δ3.67-3.61 (m, 3H, CHOH & CH$_2$OH), 3.50-3.42 (m, 1H, CHOH), 1.27 (d, J=6.1 Hz, 3H, CH$_3$), 0.75 (s, 3H, CH$_3$). $^{13}$C NMR (CDCl$_3$): δ72.45 (CHOH), 70.84 (CHOH), 60.78 (CH$_2$OH), 14.03 (CH$_3$). Elemental Analysis: For C$_{18}$H$_{32}$O$_3$. Calcd: C, 72.93; H, 10.88. Found: C, 73.00; H, 10.68. Structure:

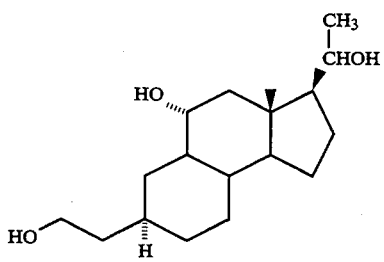

EXAMPLE 6

PREPARATION OF

[3S-[3α(S*),3aα,5β,5aβ,7α,9aα,9bβ]]-Dodecahydro-3-(1-hydroxyethyl)-7-[2-(trimethylacetyloxy)ethyl]-3a-methyl-1H-benz[e]inden-5-ol The mixture of the compound of Example 5 (750 mg, 2.5 mmol), 3-pivaloylthiazolidine-2-thione (3.4 g, 17 mmol) and NaH (240 mg, 10 mmol) in dry THF (100 ml) was stirred at 55°–60° C. for 10 h under nitrogen. Then the mixture was diluted with EtOAc (100 mL) and washed with satd. NH$_4$Cl (50 mL) and brine (50 mL). The organic layer was dried over Na$_2$SO$_4$ and the solvent was removed to give an oil. The crude product was purified by chromatography (50% EtOAc in hexane) to give the product (523 mg, 70%) as white crystals (from Et$_2$O-hexane) which had: mp 111°–113° C.

IR (film, NaCl): 3399, 2925, 1729, 1713, 1480, 1370, 1160 cm$^{-1}$. $^1$H NMR (CDCl$_3$): δ4.13–4.08 (m, 2H, CH$_2$O), 3.70–3.66 (m, 1H, CHOH), 3.53–3.44 (m, 1H, CHOH), 1.24 (d, J=6.2 Hz, 3H, CH$_3$), 1.19 (s, 9H, C(CH$_3$)$_3$), 0.69 (s, 3H, CH$_3$). $^{13}$C NMR (CDCl$_3$): δ178.60 (CO), 71.61 (CHOH), 70.00 (CHOH), 62.49 (CH$_2$O), 27.07 (C(CH$_3$)$_3$), 13.67 (CH$_3$). Elemental Analysis: For C$_{23}$H$_{40}$O$_4$. Calcd: C, 72.59; H, 10.59. Found: C, 72.73; H, 10.52. Structure:

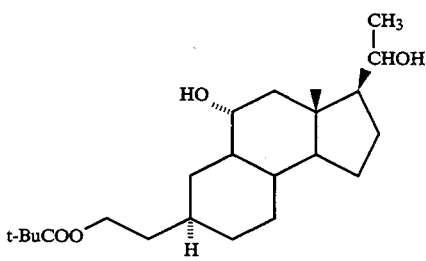

EXAMPLE 7

PREPARATION OF

[3S-(3α,3aα,5aβ,7α,9aα,9bβ)]-3-Acetyl-7-[2-(trimethylacetyloxy)ethyl]dodecahydro-3a-methyl-5H-benz[e]inden-5-one To a solution of the compound of Example 6 (420 mg, 1.1 mmol) in acetone (100 mL) was added Jones reagent (8N solution, 0.5 mL) with stirring at −5° C. After 5 min, the reaction was quenched with isopropanol (1.0 mL), and EtOAc (50 mL) and H$_2$O (50 mL) were added. The aqueous layer was extracted with EtOAc (2×50 mL) and the combined organic layers were washed with satd. NaHCO$_3$ (50 mL) and brine (50 mL) and dried over Na$_2$SO$_4$. The solvent was removed to give a solid, which was recrystallized from Et$_2$O-hexane to give the product (384 mg, 92%) as white crystals: mp 107°–109° C.

IR (film, NaCl): 2926, 1725, 1707, 1480, 1361, 1284, 1159 cm$^{-1}$. $^1$H NMR (CDCl$_3$): δ4.10 (t, J=6.6 Hz, 2H, CH$_2$O), 2.77 (t, J=9.1 Hz, 1H, CHC(=O)CH$_3$), 2.11 (s,3H, CH$_3$), 1.19 (s, 9H, C(CH$_3$)$_3$), 0.59 (s, 3H, CH$_3$). $^{13}$C NMR (CDCl$_3$): δ210.59 (CO), 208.01 (CO), 178.47 (CO), 62.30 (CH$_2$O), 27.12 (C(CH$_3$)$_3$), 14.56 (CH$_3$). Elemental Analysis: For C$_{23}$H$_{36}$O$_4$. Calcd: C, 73.37; H, 9.64. Found: C, 73.55; H, 9.47. Structure:

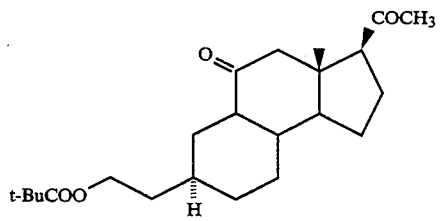

EXAMPLE 8

PREPARATION OF

[3R-(3α,3aβ,5aα,7β,9aβ,9b α)]-3-Acetyldodecahydro-7-(2-hydroxyethyl)-3a-methyl-5H-benz[e]inden-5-one (8a) and

[3S-(3α,3aα,5aβ,7α,9aα,9b β)]-3-Acetyldodecahydro-7-(2-hydroxyethyl)-3a-methyl-5H-benz[e]inden-5-one (8b)

A solution of the compound of Example 7 (180 mg, 0.48 mmol) and 3N aq. KOH (20 mL) in MeOH (20 mL) was stirred at room temperature for 60 h under nitrogen. Then the mixture was acidified to pH 2 with 3N aq. HCl at 0° C. The mixture was extracted with EtOAc (3×50 mL) and the combined organic layers were washed with brine (50 mL) and dried over Na$_2$SO$_4$. The solvent was removed to give a yellow oil which was purified by chromatography (60% EtOAc in hexane) to give an isomeric mixture of products 8a and 8b (116 mg, 83%) as an oil which was separated completely by HPLC (silica, 60% EtOAc in hexane, 3.3 mL/min).

Compound 8a (24.9 mg, 21%) was obtained as colorless crystals: mp 55°–55.5° C. (from Et$_2$O/hexane). IR (film, NaCl): 3403, 2926, 1704, 1445, 1360, 1270, 1225, 1176, 1056 cm$^{-1}$. $^1$H NMR (CDCl$_3$): δ3.72 (t, J=6.6 Hz, 2H, OCH$_2$), 2.83 (dd, J=2.5 Hz, J=5.9 Hz, 1H, CH(C=O)CH$_3$), 2.13 (s, 3H, COCH$_3$), 0.85 (s, 3H, CH$_3$). $^{13}$C NMR (CDCl$_3$): δ212.22 (CO), 211.60 (CO), 60.40 (CH$_2$O), 21.92 (CH$_3$). Elemental Analysis: For C$_{18}$H$_{28}$O$_3$. Calcd: C, 73.93; H, 9.65. Found: C, 73.90; H, 9.50. Structure:

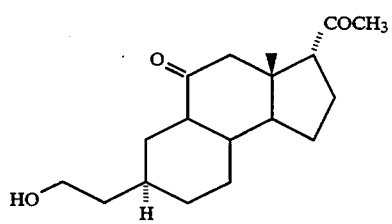

Compound 8b (58 mg, 41%) was obtained as colorless crystals: mp 84.5°–86.5° C. (from diethyl ether). IR (film, NaCl): 3383, 2923, 1703, 1445, 1360, 1268, 1225, 1055 cm$^{-1}$. $^1$H NMR (CDCl$_3$): δ3.72 (t, J=6.5 Hz, 2H, OCH$_2$), 2.77 (t, J=9.1 Hz, 1H, CH(C=O)CH$_3$), 2.11 (s, 3H, COCH$_3$), 0.60 (s, 3H, CH$_3$). $^{13}$C NMR (CDCl$_3$): δ211.08 (CO), 208.29 (CO), 61.90 (CH$_2$O), 14.37 (CH$_3$). Elemental Analysis: For C$_{18}$H$_{28}$O$_3$. Calcd: C, 73.93; H, 9.65. Found: C, 73.97; H, 9.57. Structure:

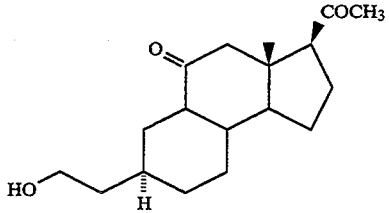

EXAMPLE 9

PREPARATION OF

[3S-[3α(S*),3aα,5β,5aβ,7β,9aα,9bβ]]-Dodecahydro-3-(1-hydroxyethyl)-7-(2-hydroxyethyl)-3a-methyl-1H-benz[e]inden-5-ol Using compound 4b (1.0 g, 2.3 mmol) and the same reduction procedure reported in Example 5, a solid was obtained which was purified by recrystallization from MeOH-EtOAc to yield the product (620 mg, 91%) as white crystals which had: mp 174°–176° C.

IR (film, NaCl): 3392, 2931, 1451, 1371, 1048 cm$^{-1}$. $^1$H NMR (CDCl$_3$): δ3.63–3.54 (m, 3H, CHOH & CH$_2$OH), 3.43–3.32 (m, 1H, CHOH), 1.21 (d, J=6.2 Hz, 3H, CH$_3$), 0.70 (s, 3H, CH$_3$). $^{13}$C NMR (CDCl$_3$): δ72.41 (CHOH), 70.78 (CHOH), 61.60 (CH$_2$OH), 14.12 (CH$_3$). Elemental Analysis: For C$_{18}$H$_{32}$O$_3$. Calcd: C, 72.93; H, 10.88. Found: C, 72.75; H, 10.68. Structure:

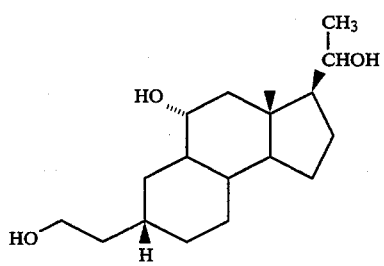

EXAMPLE 10

PREPARATION OF

[3S-[3α(S*),3aα,5β,5aβ,7β,9aα,9bβ]]-Dodecahydro-3-(1-hydroxyethyl)-7-[2-(trimethylacetyloxy)ethyl]-3a-methyl-1H-benz[e]inden-5-ol Using the selective esterification procedure described in Example 6 on the compound of Example 9 (592 mg, 2.0 mmol), a solid was obtained which was purified by recrystallization from Et$_2$O-hexane to yield the product (585 mg, 77%) as white crystals which had: mp 81°–83° C.

IR (film, NaCl): 3379, 2917, 1728, 1712, 1480, 1369, 1164 cm$^{-1}$. $^1$H NMR (CDCl$_3$): δ4.12–4.05 (m, 2H, CH$_2$O), 3.71–3.66 (m, 1H, CHOH), 3.55–3.43 (m, 1H, CHOH), 1.24 (d, J=6.2 Hz, 3H, CH$_3$), 1.19 (s, 9H, C(CH$_3$)$_3$), 0.70 (s, 3H, CH$_3$). $^{13}$C NMR (CDCl$_3$): δ178.74 (CO), 71.75 (CHOH), 70.11 (CHOH), 63.41 (CH$_2$O), 27.14 (C(CH$_3$)$_3$), 13.75 (CH$_3$). Elemental Analysis: For C$_{23}$H$_{40}$O$_4$. Calcd: C, 72.59; H, 10.59. Found C, 72.70; H, 10.64. Structure:

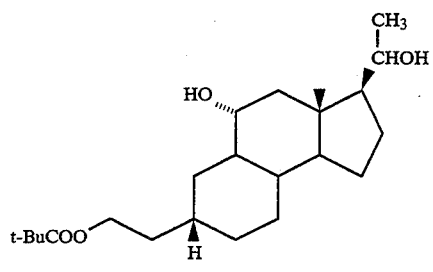

EXAMPLE 11

PREPARATION OF

[3S-(3α,3aα,5aβ,7β,9aα,9bβ)]-3-Acetyl-7-[2-(trimethylacetyloxy)ethyl]dodecahydro-3a-methyl-5H-benz[e]inden-5-one Using the oxidation procedure of Example 7 on the compound of Example 10 (350 mg, 0.92 mmol), a solid was obtained which was purified by recrystallization from Et$_2$O to yield the product (320 mg, 93%) as white crystals which had: mp 121°–123° C.

IR (film, NaCl): 2928, 1726, 1706, 1480, 1361, 1285, 1158 cm$^{-1}$. $^1$H NMR (CDCl$_3$): δ4.06 (t, J=6.8 Hz, 2H, CH$_2$O), 2.79 (t, J=9.2 Hz, 1H, CH(C=O)CH$_3$), 2.12 (s, 3H, CH$_3$), 1.19 (s, 9H, C(CH$_3$)$_3$), 0.60 (s, 3H, CH$_3$). $^{13}$C NMR(CDCl$_3$): δ210.90 (CO), 207.93 (CO), 178.36 (CO), 63.08 (CH$_2$O), 26.99 (C(CH$_3$)$_3$), 14.46 (CH$_3$). Elemental Analysis: For C$_{23}$H$_{36}$O$_4$. Calcd: C, 73.37; H, 9.64. Found: C, 73.38; H, 9.54. Structure:

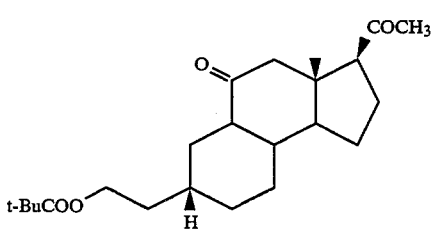

EXAMPLE 12

PREPARATION OF

[3R-(3α,3aβ,5aα,7α,9aβ,9bα)]-3-Acetyldodecahydro-7-(2-hydroxyethyl)-3a-methyl-5H-benz[e]inden-5-one (12a) and

[3S-(3α,3aα,5aβ,7β,9aα,9bβ)]-3-Acetyldodecahydro-7-(2-hydroxyethyl)-3a-methyl-5H-benz[e]inden-5one (12b)

Using the procedure of Example 8 on the compound of Example 11 (200 mg, 0.53 mmol), a mixture of isomeric products 12a and 12b (in the ratio of ~1:4) was obtained as an oil (100 mg, 64%) which was purified by chromatography (silica, 80% EtOAc in hexane) and then was separated completely by HPLC (silica, 70% EtOAc in hexane, 3.0 mL/min).

Compound 12a (30 mg, 19%) was obtained as colorless crystals: mp 159°–160° C. (from diethyl ether). IR (film, NaCl): 3406, 2925, 1702, 1447, 1361, 1270, 1229, 1184, 1054 cm$^{-1}$. $^1$H NMR (CDCl$_3$): δ3.63 (t, J=6.7 Hz, 2H, CH$_2$OH), 2.83 (dd, J=2.6 Hz, J=5.5 Hz, 1H, CH(C=O)CH$_3$), 2.13 (s, 3H, COCH$_3$), 0.85 (s, 3H, CH₃). ¹³C NMR (CDCl₃): δ212.09 (CO), 211.84 (CO), 61.37 (CH₂OH), 21.97 (CH₃). Elemental Analysis: For C₁₈H₂₈O₃. Calcd: C, 73.93; H, 9.65. Found: C, 73.77; H, 9.60. Structure:

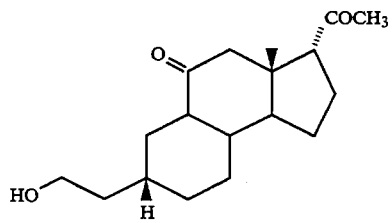

Compound 12b (70 mg, 45%) was obtained as colorless crystals, mp 82°-83° C. (from diethyl etherhexane). IR (film, NaCl): 3482, 2924, 1703, 1447, 1361, 1270, 1229, 1054 cm⁻¹. ¹H NMR (CDCl₃): δ3.65 (t, J=6.9 Hz, 2H, CH₂OH), 2.78 (t, J=9.1 Hz, 1H, CH(C=O)CH₃), 2.12 (s, 3H, COCH₃), 0.59 (s, 3H, CH₃). ¹³C NMR (CDCl₃): δ211.23 (CO), 208.15 (CO), 62.19 (CH₂O), 14.53 (CH₃). Elemental Analysis: For C₁₈H₂₈O₃. Calcd: C, 73.93: H, 9.65. Found: C, 73.76; H, 9.42. Structure:

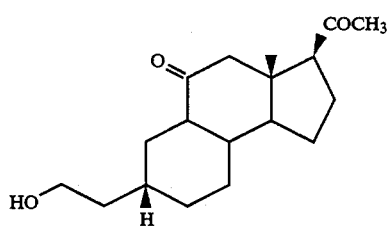

EXAMPLE 13

PREPARATION OF [3S-(3α,3aα,5aβ,9aα,9bβ)]-3-(1,1-Dimethylethoxy)dodecahydro-3a-methyl-7H-benz[e]inden-7-one Liquid ammonia (ca 800 mL) was condensed in a 2 L, 3-necked round bottom flask at −78° C. Toluene (160 mL) and THF (160 mL) were added with stirring, and Li wire (1.52 g, 219 mmol) was added. When all the Li was dissolved, a solution of [3S-(3α,3aα,9aα,9bβ)]-3-(1,1-Dimethylethoxy)-1,2,3,3a,4,5,8,9,9a,9b-decahydro-3a-methyl-7H-benz[e]inden-7-one (13.31 g, 48.1 mmol) in toluene (80 mL) and THF (80 mL) was added slowly. The deep blue reaction mixture was stirred for another 40 min and then 1,2-dibromoethane was added dropwise to discharge the blue color. A solution of HOAc (20 mL) in MeOH (80 mL) was added dropwise over 20 min and the NH₃ was allowed to evaporate. The mixture was diluted with water (800 mL) and EtOAc (400 mL), and the organic layer was separated. The water layer was extracted with EtOAc (400 mL). The combined organic layers were washed with brine (2×400 mL) and dried over Na₂SO₄. The solvent was removed to give an oil which was purified by chromatography (silica gel, 15% EtOAc in hexane) to give 5.84 g (44%) of the product as colorless crystals: mp 98°-99° C. (from absolute EtOH).

IR (film, NaCl): 2967, 2869, 1711, 1454, 1387, 1361, 1195, 1072, 1026 cm⁻¹. ¹H NMR (CDCl₃): δ3.41 (t, J=8.2 Hz, 1H, CHOC(CH₃)₃), 1.13 (s, 9H, C(CH₃)₃), 0.80 (s, 3H, CH₃). ¹³C NMR(CDCl₃): δ211.61 (C=O), 80.44 (C³), 72.18 (C(CH₃)₃), 28.67 (C(CH₃)₃), 11.65 (CH₃). Elemental Analysis: For C₁₈H₃₀O₂. Calcd: C, 77.65; H, 10.86. Found: C, 77.75; H, 10.61. Structure:

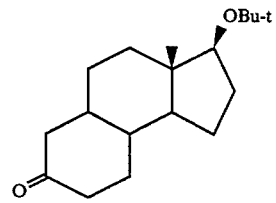

EXAMPLE 14

PREPARATION OF [3S-(3α,3aα,5aβ,7Z,9aα,9bβ)]-3-(1,1-Dimethylethoxy)dodecahydro-7-(ethoxycarbonylmethylene)-3a-methyl-1H-benz[e]indene (14Z) and

[3S-(3α,3aα,5aβ,7E,9aα,9bβ)]-3-(1,1-Dimethylethoxy)dodecahydro-7-(ethoxycarbonylmethylene)-3a-methyl-1H-benz[e]indene (14E)

The compound of Example 13 (5.54 g, 19.9 mmol) and (carbethoxymethylene)triphenylphosphorane (13.87 g, 39.8 mmol) were heated to 160° C. overnight (ca 17 h) under nitrogen with stirring. The resultant brown colored liquid was cooled to room temperature and EtOAc (200 mL) was added. The solution was washed with water (200 mL) and brine (200 mL) and dried over Na₂SO₄. The organic layer was evaporated under reduced pressure to yield a gum which was purified by chromatography (silica gel, 5% EtOAc in hexane) to give 14Z and 14E (6.8 g, 98%) as an oil which was separated by HPLC (silica gel, 2.5% EtOAc in hexane, 3 mL/min) to give 14Z (first fraction) and 14E (second fraction).

Compound 14Z was obtained as white crystals: mp 56°-58° C. IR (film, NaCl): 2974, 2928, 1717, 1647, 1447, 1379, 1362, 1199, 1155, 1043, 903, 865 cm⁻¹. ¹H NMR (CDCl₃): δ5.60 (s, 1H, CH=), 4.14 (q, J=7.1 Hz, 2H, OCH₂CH₃), 3.38 (t, J=8.2 Hz, 1H, CHOC(CH₃)₃), 1.27 (t, J=7.1 Hz, 3H, CH₃CH₂), 1.12 (s, 9H, C(CH₃)₃), 0.77 (s, 3H, CH₃). ¹³C NMR (CDCl₃): δ166.84 (C=O), 162.94 (C=), 80.62(C³), 72.14 (CH₃)₃), 59.43 (OCH₂), 28.70(C(CH₃)₃), 11.72 (CH₃). Elemental Analysis: For C₂₂H₃₆O₃. Calcd: C, 75.82; H, 10.41. Found: C, 76.00; H, 10.21. Structure:

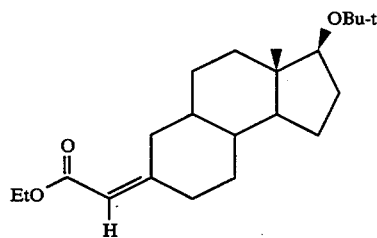

Compound 14E was obtained as an oil. IR (film, NaCl): 2974, 2922, 1718, 1650, 1446, 1380, 1361, 1199, 1173, 1045, 894, 851 cm⁻¹. ¹H NMR (CDCl₃): δ5.59 (s, 1H, CH=), 4.14 (q, J=7.1 Hz, 2H, OCH₂CH₃), 3.37 (t, J=8.2 Hz, 1H, CHOC(CH₃)₃), 1.27 (t, J=7.1 Hz, 3H, CH₃CH₂), 1.13 (s, 9H, C(CH₃)₃), 0.77 (s, 3H, CH₃). ¹³C NMR (CDCl₃): δ166.89 (C=O), 162.91 (C=), 113.10 (C=), 80.62(C³), 72.14 (C(CH₃)₃), 59.44 (OCH₂), 28.70 (C(CH₃)₃), 11.72 (CH₃). Elemental Analysis:

C₂₂H₃₆O₃. Calcd: C, 75.82; H, 10.41. Found: C, 76.01; H, 10.25. Structure:

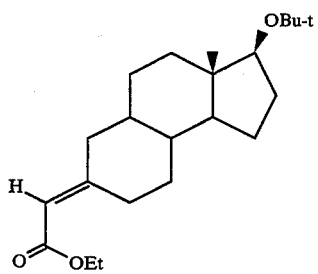

EXAMPLE 15
PREPARATION OF

[3S-(3α,3aα, 5aβ, 9bβ)]-3-(1,1-Dimethylethoxy)dodecahydro-3a-methyl-1H-benz[e]indene-7-acetic acid ethyl ester Palladium on calcium carbonate (5.96 g, palladium content 5%) was added to a solution of unseparated 14Z and 14E (5.96 g) of Example 14 in N-methylpyrrolidine (150 mL) in a glass bottle used for a Parr hydrogenation apparatus. The hydrogenation was carried out overnight at room temperature with ca 40–50 psi of hydrogen. The catalyst was filtered off, the solvent was moved under reduced pressure, and the product was purified by chromatography (silica gel, 2.5% EtOAc in hexane) to give the product (5.86 g, 98%) as an oil.

IR (film, NaCl): 2906, 1733, 1447, 1361, 1276, 1199, 1074, 1031, 906 cm⁻¹. ¹H NMR (CDCl₃): δ4.12 (q, J=7.1 Hz, 2H, OCH₂), 3.38 (t, 1H, J=8.2 Hz CHOC(CH₃)₃), 1.25 (t, J=7.2 Hz, 3H, CH₃CH₂), 1.12 (s, 9H, C(CH₃)₃), 0.73 (s, 3H, CH₃). ¹³C NMR (CDCl₃): δ173.60 (C=O), 173.17 (C=), 80.82 (C³), 72.07 (C(CH₃)₃), 60.04 (OCH₂CH₃), 49.83 (CH₂COOEt), 28.71 (C(CH₃)₃), 11.70 (CH₃). Elemental Analysis: For C₂₂H₃₈O₃. Calcd: C, 75.38; H, 10.93. Found: C, 75.12; H, 10.76 Structure:

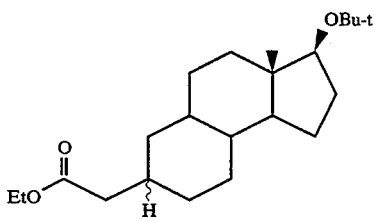

EXAMPLE 16
PREPARATION OF

[3S-(3α,3aα,5aβ,7Z,9aα,9bβ)]-3-(1,1-Dimethylethoxy)-dodecahydro-7-(2-hydroxyethylidene)-3a-methyl-1H-benz[e]indene (16Z)

[3S-(3α,3aα,5aβ,7E,9aα,9bβ)]-3-(1,1-Dimethylethoxy)-dodecahydro-7-(2-hydroxyethylidene)-3a-methyl-1H-benz[e]indene (16E)

To a stirred solution of unseparated compounds 14Z and 14E of Example 14 (6.59 g, 18.9 mmol) in dry dichloromethane (100 mL) was added diisobutylaluminium hydride (1.0M solution in toluene, 75.7 mL, 75.7 mmol) at 0° C. After 36 h, dichloromethane/methanol (1:1, v/v, 100 mL) and then aq. 10% HCl (50 mL) were added. The separated organic layer was washed with 0.3N NaOH (200 mL) and brine (400 mL) and dried over Na₂SO₄. After filtration, the solvent was removed under reduced pressure to give an oil which was purified by chromatography (silica gel, 15% EtOAc in hexane) to give products 16Z and 16E as an oil (5.00 g, 86%). The product mixture was separated by HPLC (silica gel, 10% EtOAc in hexane, 3 mL/min) to yield 16Z (first fraction) and 16E (second fraction).

Compound 16Z was obtained as a colorless oil. IR (film, NaCl): 3368, 2921, 2868, 1668, 1360, 1196, 1133, 1092, 902 cm⁻¹. ¹H NMR (CDCl₃): δ5.35 (t, J=7.1 Hz, 1H, HC=), 4.13 (d, J=7.1 Hz, 2H, HOCH₂), 3.36 (t, J=8.2 Hz, 1H, CHOC(CH₃)₃), 1.12 (s, 9H, C(CH₃)₃), 0.75 (s, 3H, CH₃). ¹³C NMR (CDCl₃): δ143.85 (C=), 120.35 (C=), 80.76 (C³), 72.11 (C(CH₃)₃), 58.52 (HOCH₂), 28.72 (C(CH₃)₃), 11.73 (CH₃). Structure:

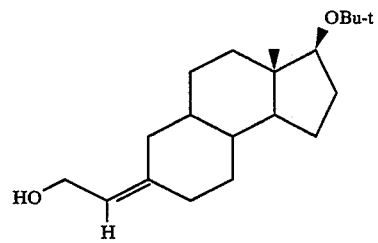

Compound 16E was obtained as white crystals: mp 108°–110° C. (from EtOAc/hexane). IR (film, NaCl): 3372, 2921, 2867, 1669, 1361, 1198, 1133, 1095, 949, 899, 990 cm⁻¹. ¹H NMR (CDCl₃): δ5.35 (t, J=7.1 Hz, 1H, HC=), 4.13 (d, J=7.0 Hz, 2, HOCH₂), 3.36 (t,J=8.2 Hz, 1H, CHOC(CH₃)₃), 1.12 (s, 9H, C(CH₃)₃), 0.75 (s, 3H, CH₃). ¹³C NMR (CDCl₃): δ143.90 (C=), 120.49 (C=), 80.76 (C³), 72.12 (C(CH₃)₃), 61.79 (HOCH₂), 28.73 (C(CH₃)₃), 11.73 (CH₃). Elemental Analysis: For C₂₀H₃₄O₂. Calcd: C, 78.38; H, 11.18; Found: C, 78.17; H, 11.10. Structure:

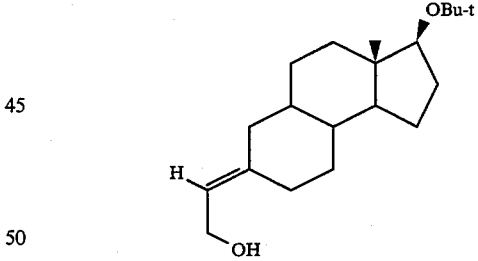

EXAMPLE 17
PREPARATION OF

[3S-(3α,3aα,5aβ,7β,9aα,9bβ)]-3-(1,1-Dimethylethoxy)-dodecahydro-3a-methyl-N-[(S)-1-phenylethyl]-1H-benz[e]indene-7-acetamide (17a)

[3S-(3α,3aα,5aβ,7α,9aα,9bβ)]-3-(1,1-Dimethylethoxy)-dodecahydro-3a-methyl-N-[(S)-1-phenylethyl]-1H-benz[e]indene-7-acetamide (17b)

The compound of Example 15 (7.30 g, 20.8 mmol), 20% NaOH (10 mL), EtOH (30 mL) and H₂O (10 mL) were refluxed in an oil bath for 1 h. The solution was cooled with ice water, neutralized with 3M HCl to pH=2–3, and extracted with EtOAc (3×100 mL). The combined organic layers were washed with brine (2×200 mL) and water (100 mL) and dried with Na₂SO₄. The solvent was evaporated under reduced pressure to give an oil (6.6 g, 98%).

To a portion of the oil (3.89 g, 12.1 mmol) dissolved in dry benzene (100 mL) and dry DMF (8 mL) was added 1,1'-carbonyldiimidazole (3.94 g, 24.3 mmol) under nitrogen gas. The reaction was stirred at room temperature for 1 hr, then HOAc (732 mg, 12.2 mmol) was added. After 10 min., (S)-(−)-α-phenylethylamine (4.44 g, 36.6 mmol) was added. After an additional 2 h, the solution was evaporated to about 10 mL and chromatographed (silica gel, 25% EtOAc in hexane) to give products 17a and 17b as an oil (4.55 g, 89%). A portion of this oil (3.0 g) was separated by preparative scale HPLC (silica gel, 35.6% EtOAc in hexane, 250 mL/min) to give 17a (1.36 g first fraction) and 17b (1.41 g second fraction).

Compound 17a was obtained as colorless crystals: mp 175°–177° C. (from EtOAc/hexane). IR (film, NaCl): 3277, 3061, 2973, 2852, 1637, 1542, 1361, 1199, 1134, 1082, 908, 735 cm$^{-1}$. $^1$H NMR (CDCl$_3$): δ7.39–7.27 (m, 5H, C$_6$H$_5$), 5.72 (d,J=9.0 Hz, 1H, NH), 5.17–5.13 (m, 1H, NCHCH$_3$), 3.36 (t,J=8.2 Hz, 1H, CHOC(CH$_3$)$_3$), 2.24 (d,J=7.6 Hz, 2H, CH$_2$), 1.48 (d,J=6.8 Hz, 3H, NCHCH$_3$), 1.12 (s, 9H, C(CH$_3$)$_3$), 0.73 (s, 3H, CH$_3$). $^{13}$C NMR (CDCl$_3$): δ171.87 (C=O), 143.20 (Arom. C), 128.61 (Arom. C), 127.29 (Arom. C), 126.14 (Arom. C), 80.81 (C$^3$), 72.10 (C(CH$_3$)$_3$), 28.71 (C(CH$_3$)$_3$), 11.74 (CH$_3$). Elemental Analysis: For C$_{28}$H$_{43}$NO$_2$. Calcd: C, 79.01; H, 10.18; N, 3.29. Found: C, 79.07; H, 9.96, N, 3.27. Structure:

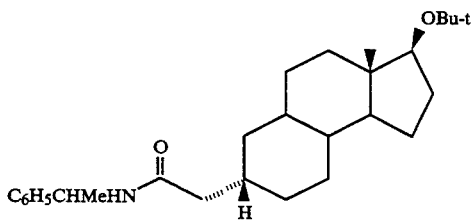

Compound 17b was obtained as colorless crystals: mp 145°–146° C. (EtOAc/hexane). IR (film, NaCl): 3277, 3063, 2914, 1638, 1542, 1361, 1199, 1141, 1074, 909, 732, 700 cm$^{-1}$. $^1$H NMR (CDCl$_3$): δ7.33–7.25 (m, 5H, C$_6$H$_5$), 5.86 (d,J=7.3 Hz, 1H, NH), 5.16–5.11 (m, 1H, NCHCH$_3$), 3.37 (t,J=8.2 Hz, 1H, CHOC(CH$_3$)$_3$), 2.05–2.02 (m, 2H, CH$_2$), 1.48 (d,J=7.0 Hz, 3H, NCHCH$_3$), 1.12 (s, 9H, C(CH$_3$)$_3$), 0.72 (s, 3H, CH$_3$). $^{13}$C NMR (CDCl$_3$): δ171.57 (C=O), 143.21 (Arom. C), 128.57 (Arom. C), 127.28 (Arom. C), 126.17 (Arom. C), 80.81 (C$^3$), 72.08 (C(CH$_3$)$_3$), 28.72 (C(CH$_3$)$_3$), 11.71 (CH$_3$). Elemental Analysis: For C$_{28}$H$_{43}$NO$_2$. Calcd: C, 79.01; H, 10.18; N, 3.29. Found: C, 79.01; H, 9.72; N, 3.06. Structure:

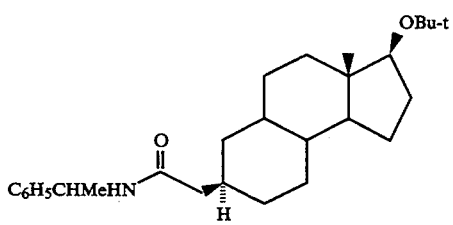

EXAMPLE 18

PREPARATION OF

[3S-(3α,3aα,5aβ,7α,9aα,9bβ)]-3-(1,1-Dimethylethoxy)-dodecahydro-3a-methyl-H-benz[e]indene-7-acetic acid To a stirred solution of compound 17b (0.63 g, 1.48 mmol) of Example 17 in HOAc (5 mL) acetic anhydride (25 mL) at 0° C. was added (1 h addition time) NaNO$_2$ (2.61 g, 37.84 mmol). The was kept at 0° C. overnight. The mixture was then extracted with ether (2×80 mL), and the extracts were washed with water (100 mL), satd. NaHCO$_3$ (100 mL), brine (100 mL), and dried Na$_2$SO$_4$. The solvent was removed under reduced pressure to give a residue. Dioxane (100 mL) was and the reaction was refluxed overnight. The dioxane was removed under reduced pressure and NaOH (30 mL) and EtOH (25 mL) were added. The reaction was refluxed for 1 h, cooled with ice acidified with 3M HCl to pH=1-2, and extracted with EtOAc (2×150 mL). The combined organic were washed with water (150 mL) and brine (150 mL) and dried with Na$_2$SO$_4$. Solvent removal which was purified by chromatography (silica gel, 50% EtOAc and 1% HOAc in hexane) to product (0.42 g, 80%) as white crystals: mp 139°–140° C.

IR (film, NaCl): 2916, 1704, 1447, 1412, 1382, 1359, 1300, 1201, 1076, 1029, 951 cm$^{-1}$. $^1$H NMR (CDCl$_3$): δ3.38 (t,J=8.3 Hz, 1H, CHOC(CH$_3$)$_3$), 2.22 (d,J=7.0 Hz, 2H, CH$_2$COO 1.13 (s, 9H, C(CH$_3$)$_3$), 0.73 (s, 3H, CH$_3$). $^{13}$C NMR (CDCl$_3$): δ179.43 (C=O), 80.87 (C$^3$), 72.16 (C(CH$_3$)$_3$), 28.74 (C(CH$_3$)$_3$), 11.74 (CH Elemental Analysis: For C$_{20}$H$_{34}$O$_3$. Calcd: C, 74.49; H, 10.63. Found: C, 74.56; H, 10.47. Structure:

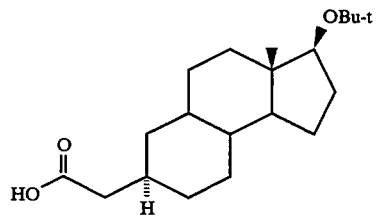

EXAMPLE 19

PREPARATION OF

[3S-(3α,3aα,5aβ,7α,9aα,9bβ)]-3-(1,1-Dimethylethoxy)-dodecahydro-3a-methyl-1H-benz[e]indene-7-acetic acid methyl ester Diazomethane in EtOH and ether at 0° C. was added to a stirred solution of the compound of Example 18 (150 mg, 0.47 mmol) in EtOAc (5 mL) and EtOH (10 mL) until a yellow color persisted. The solution was allowed to stir for an additional 5 min. Excess diazomethane was destroyed by the addition of several drops of formic acid. The solution was evaporated to near dryness under reduced pressure and purified by chromatography (silica gel, 5% EtOAc in hexane) to give the product (150 mg, 96%) as white crystals: mp 47°–48° C.

IR (film, NaCl): 2915, 1741, 1445, 1390, 1361, 1277, 1200, 1156, 1074, 1029, 895 cm$^{-1}$. $^1$H NMR (CDCl$_3$): δ3.66 (s, 3H, CH$_3$O), 3.37 (t,J=8.2 Hz, 1H, CHOC(CH$_3$)$_3$), 2.19 (d,J=6.9 Hz, 2H, CH$_2$COOMe), 1.12 (s, 9H, C(CH$_3$)$_3$), 0.73 (s, 3H, CH$_3$). $^{13}$C NMR (CDCl$_3$): δ173.45 (C=O), 80.79 (C$^3$), 71.99 (C(CH$_3$)$_3$), 28.69 (C(CH₃)₃), 11.68 (CH₃). Elemental Analysis: For $C_{21}H_{36}O_3$. Calcd: C, 74.95; H, 10.78. Found: C, 74.78; H, 10.69. Structure:

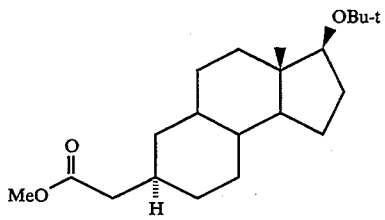

EXAMPLE 20

PREPARATION OF

[3S-(3α,3aα,5aβ,7β,9aα,9bβ)]-3-(1,1-Dimethylethoxy)-dodecahydro-3a-methyl-1H-benz[e]indene-7-acetic acid methyl ester To a stirred solution of compound 17a (1.74 g, 4.09 mmol) of Example 17 in HOAc (15 mL) and acetic anhydride (30 mL) at 0° C. was added (1 h addition time) NaNO₂ (6.12 g, 88.7 mmol). The reaction was kept at 0° C. overnight. The mixture was then extracted with ether (2×150 mL), and the combined extracts were washed with water (200 mL), satd. NaHCO₃ (200 mL), brine (200 mL), and dried over Na₂SO₄. The organic layer was removed under reduced pressure to give a residue. Dioxane (100 mL) was added and the reaction was refluxed overnight. The dioxane was removed under reduced pressure and aq. 20% NaOH (50 mL) and EtOH (50 mL) were added. The reaction was refluxed for 1 h, cooled with ice-water, acidified with 3M HCl to pH=1-2, and extracted with EtOAc (2×200 mL). The combined organic layers were washed with water (200 mL) and brine (300 mL) and dried with Na₂SO₄. Solvent removal gave an oil which was purified by chromatography (silica gel, 50% EtOAc and 1% HOAc in hexane) to give [3S-(3α,3aα,-5aβ,7β,9aα,9bβ)]-3-(1,1-Dimethylethoxy)dodecahydro-3a-methyl-1H-benz[e]indene-7-acetic acid (1.19 g, 90%). This product was dissolved in EtOAc (20 mL) and EtOH (10 mL) and treated with a solution of diazomethane in EtOH and ether at 0° C. until a yellow color persisted. The solution was allowed to stir for an additional 15 min. Excess diazomethane was destroyed by the addition of several drops of formic acid. The solution was evaporated to near dryness under reduced pressure and purified by chromatography (silica gel, 5% EtOAc in hexane) to give the product (1.16 g, 93%) as white crystals: mp 55°-57° C.

IR (film, NaCl): 2914, 1743, 1437, 1360, 1276, 1198, 1131, 1083, 1031, 988, 904 cm⁻¹. ¹H NMR (CDCl₃): δ3.66 (s, 3H, CH₃O), 3.37 (t,J=8.2 Hz, 1H, CHOC(CH₃)₃), 2.41-2.34 (m, 2H, CH₂COOMe), 1.12 (s, 9H, C(CH₃)₃), 0.73 (s, 3H, CH₃). ¹³C NMR (CDCl₃): δ173.90 (C=O), 80.76 (C³), 71.98 (C(CH₃)₃), 28.65 (C(CH₃)₃), 11.68 (CH₃). Elemental Analysis: For $C_{21}H_{36}O_3$. Calcd: C, 74.95; H, 10.78. Found: C, 75.18; H, 10.80. Structure:

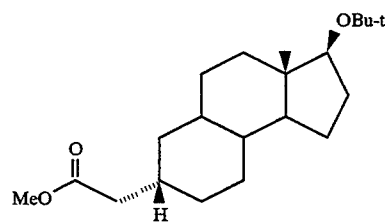

EXAMPLE 21

PREPARATION OF

[3S-(3α,3aα,5aβ,7α,9aα,9bβ)]-3-(1,1-Dimethylethoxy)-dodecahydro-3a-methyl-1H-benz[e]indene-7-ethanol To a stirred solution of the compound of Example 19 (150 mg, 0.45 mmol) in dry dichloromethane (5 mL) was added diisobutylaluminium hydride (1.0M solution in hexane, 2.7 mL, 2.7 mmol) at 0° C. After 2 h, dichloromethane/methanol (1:1, v/v, 4 mL) was added, and then aq. 10% NaOH (20 mL) was added. The solution was extracted with dichloromethane (50 mL) and the organic extract was washed with brine (50 mL) and water (50 mL) and dried over Na₂SO₄. After filtration, the solvent was removed under reduced pressure to give an oil which was purified by chromatography (silica gel, 10% EtOAc in hexane) to give the product (120 mg, 87%) as white crystals: mp 88°-89° C.

IR (film, NaCl): 3814, 3320, 2914, 1448, 1388, 1360, 1198, 1116, 1077, 1028, 905 cm⁻¹. ¹H NMR (CDCl₃): δ3.68 (t,J=6.5 Hz, 2H, HOCH₂), 3.38 (t,J=8.2 Hz, 1H, CHOC(CH₃)₃), 1.13 (s, 9H, C(CH₃)₃), 0.73 (s, 3H, CH₃). ¹³C NMR (CDCl₃): δ80.87 (C³), 72.10 (C(CH₃)₃), 60.75 (HOCH₂), 28.71 (C(CH₃)₃), 11.72 (CH₃). Elemental Analysis: For $C_{20}H_{36}O_2$. Calcd: C, 77.87; H, 11.76,. Found: C, 78.00; H, 11.72. Structure:

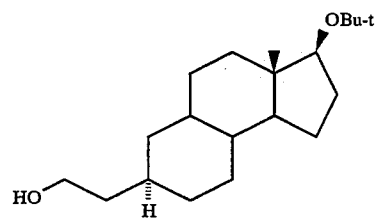

EXAMPLE 22

PREPARATION OF

[3S-(3α,3aα,5aβ,7β,9aα,9bβ)]-3-(1,1-Dimethylethoxy)-dodecahydro-3a-methyl-1H-benz[e]indene-7-ethanol To a stirred solution of the compound of Example 20 (1.70 g, 5.05 mmol) in dry dichloromethane (80 mL) was added diisobutylaluminium hydride (1.0M solution in toluene, 33.6 mL, 33.6 mmol) at 0° C. After 2 h, dichloromethane/methanol (1:1, 8 mL) was added, and then aq. 10% HCl (10 mL) was added. The organic layer was washed with 0.3N NaOH (170 mL) and brine (200 mL) and dried over Na₂SO₄. After filtration, the solvent was removed under reduced pressure to give a solid which was purified by chromatography (silica gel, 15% EtOAc in hexane) to give the product (1.51 g, 96%) as white crystals: mp 86°-87° C. (from EtOAc/hexane).

IR (film, NaCl): 3328, 2973, 2915, 2862, 1449, 1361, 1197, 1122, 1083, 990 cm$^{-1}$. $^1$H NMR (CDCl$_3$): δ3.65 (t, J=7.0 Hz, 2H, HOCH$_2$), 3.37 (t, J=8.2 Hz, 1H, CHOC(CH$_3$)$_3$), 1.13 (s, 9H, C(CH$_3$)$_3$), 0.73 (s, 3H, CH$_3$). $^{13}$C NMR (CDCl$_3$): δ80.76 (C$^3$), 72.10 (C(CH$_3$)$_3$), 61.79 (HOCH$_2$), 28.71 (C(CH$_3$)$_3$), 11.76 (CH$_3$). Elemental Analysis: For C$_{20}$H$_{36}$O$_2$. Calcd: C, 77.87; H, 11.76. Found: C, 77.91; H, 11.51. Structure:

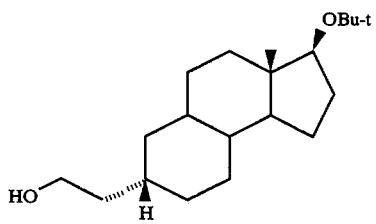

EXAMPLE 23

PREPARATION OF

[3S-(3α,3aα,5aβ,7β,9aα,9bβ)]-Dodecahydro-7-(2-hydroxyethyl)-3a-methyl-1H-benz[e]inden-3-ol A solution of the compound of Example 22 (1.5 g, 4.86 mmol) in EtOH (50 mL) and 6N HCl (15 mL) was refluxed for 1.5 h. Most of the EtOH was removed under reduced pressure and the solution was extracted with EtOAc (2×150 mL). The combined organic layers were washed with water (200 mL), satd. NaHCO$_3$ (200 mL), brine (200 mL) and dried over Na$_2$SO$_4$. After filtration, the solvent was removed under reduced pressure to give a solid which was purified by chromatography (silica gel, 35% EtOAc in hexane) to yield the product (1.20 g, 98%) as white crystals: mp 103°-104° C. (from EtOAc/hexane).

IR (film, KCl): 3293, 2916, 2856, 1656, 1448, 1382, 1138, 1061, 1022 cm$^{-1}$. $^1$H NMR (CDCl$_3$): δ369-365 (m, 3H, HOCH$_2$, CHOH), 0.76 (s, 3H, CH$_3$). $^{13}$C NMR (CD$_3$OD): δ82.52 (C$^3$), 61.70 (HOCH$_2$), 11.81 (CH$_3$). Elemental Analysis: For C$_{16}$H$_{28}$O$_2$. Calcd: C, 76.14; H, 11.18. Found: C, 76.25; H, 11.08. Structure:

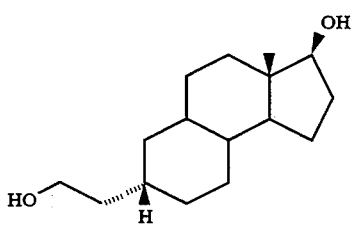

EXAMPLE 24

PREPARATION OF

[3aS-(3aα,5aβ,7β,9aα,9bβ)]-Dodecahydro-7-(2-hydroxyethyl)-3a-methyl-3H-benz[e]inden-3-one To a stirred solution of the compound of Example 23 (0.57 g, 2.26 mmol) in glacial acetic acid (10 mL) at room temperature was added dropwise within 10 min a 5.25% aq. solution of sodium hypochlorite (3.2 mL, 2.3 mmol). After 30 min, isopropanol (3 mL) was added to quench any excess oxidant and water (20 mL) was added. The mixture was extracted with EtOAc (2×150 mL). The combined organic layers were washed with water (100 mL), aq. satd. NaHCO$_3$ (100 mL), water (100 mL), brine (100 mL), and dried over Na$_2$SO$_4$. Solvent removal under reduced pressure gave a solid which was purified by chromatography (silica gel, 30% EtOAc in hexane) to give the product (0.45 g, 80%) as white crystals: mp 59°-60° C. (from EtOAc/hexane)

IR (film, NaCl): 3418, 2920, 1739, 1453, 1052 cm$^{-1}$. $^1$H NMR (CDCl$_3$): δ3.67 (t, J=6.9 Hz, 2H, HOCH$_2$), 0.89 (s, 3H, CH$_3$). $^{13}$C NMR (CDCl$_3$): δ221.53 (C=O), 61.61 (HOCH$_2$), 13.90 (CH$_3$). Elemental Analysis: For C$_{16}$H$_{26}$O$_2$. Calcd: C, 76.75; H, 10.47. Found: C, 76.76; H, 10.40. Structure:

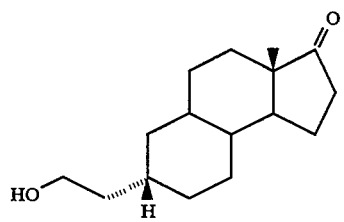

EXAMPLE 25

PREPARATION OF

[3R-(3α,3aβ,5aα,7α,9aβ,9bα)]-Dodecahydro-7-(2-hydroxyethyl)-3a-methyl-1H-benz[e]indene-3-carbonitrile (25a) and

[3S-(3α,3aα,5aβ,7β,9aα,9bβ)]-Dodecahydro-7-(2-hydroxyethyl)-3a-methyl-1H-benz[e]indene-3-carbonitrile (25b)

To a stirred solution of the compound of Example 24 (450 mg, 1.8 mmol) in dimethoxyethane (62 mL) and ethanol (2.8 mL) at room temperature was added t-BuOK (2.02 g, 18.0 mmol). A solution of tosylmethyl isocyanide (703 mg, 3.6 mmol) in dimethoxyethane (9.1 mL) was slowly (ca 10 min) added from a syringe. After 3 h, the mixture was quenched with water (50 mL) and extracted with EtOAc (3×100 mL). The combined organic layers were washed with water (2×100 mL) and brine (100 mL) and dried over Na$_2$SO$_4$. The solvent was removed to yield an oil which was purified by chromatography (silica gel, 20% EtOAc in hexane) to give products 25a (first fraction, 80 mg, 17%) and 25b (second fraction, 120 mg, 26%).

Compound 25a was obtained as white crystals: mp 97°-98° C. (from EtOAc/hexane). IR (film, NaCl): 3374, 2922, 2234, 1451, 1384, 1333, 1148, 1060, 1059 cm$^{-1}$. $^1$H NMR (CDCl$_3$): δ3.66 (t, J=6.8 Hz, 2H, HOCH$_2$), 2.57 (dd, J=6.8 Hz, J=2.0 Hz, 1H, CHCN), 0.83 (s, 3H, CH$_3$). $^{13}$C NMR (CDCl$_3$): δ122.36 (CN), 61.52 (HOCH$_2$), 50.97 (C$^3$), 18.12 (CH$_3$). Elemental Analysis: For C$_{17}$H$_{27}$NO. Calcd: C, 78.11; H, 10.41; N, 5.36. Found: C, 78.17; H, 10.51; N, 5.42 Structure:

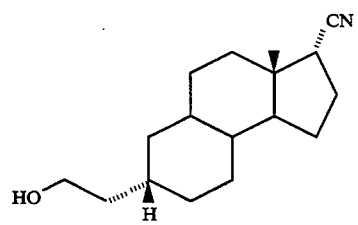

Compound 25b was obtained as white crystals: mp 61°-62° C. (from ether/hexane). IR (film, NaCl): 3374, 2919, 2236, 1450, 1386, 1061 cm$^{-1}$. $^1$H NMR (CDCl$_3$):

δ3.65 (t, J=6.9 Hz, 2H, HOCH$_2$), 2.28 (t, J=9.6 Hz, 1H, CHCN), 0.93 (s, 3H, CH$_3$). $^{13}$C NMR (CDCl$_3$): δ121.37 (CN), 61.68 (HOCH$_2$), 53.38 (C$^3$), 14.45 (CH$_3$). Elemental Analysis: For C$_{17}$H$_{27}$NO. Calcd: C, 78.11; H, 10.41; N, 5.36. Found: C, 78.29; H, 10.38; N, 5.53. Structure:

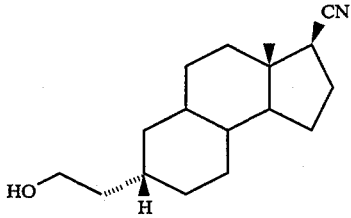

EXAMPLE 26

PREPARATION OF

[3R-(3α,3aβ,5aα,7α,9aβ,9bα)]-1-[Dodecahydro-7-(2-hydroxyethyl)-3a-methyl-1H-benz[e]inden-3-yl]-ethanone (26a) and

[3S-(3α,3aα,5aβ,7β,9aα,9bβ)]-1-[Dodecahydro-7-(2-hydroxyethyl)-3a-methyl-1H-benz[e]inden-3-yl]-ethanone (26b)

To a stirred solution of methylmagnesium chloride (3.0M, solution in THF, 5.0 mL, 15.0 mmol) cooled in an ice-water bath was added under nitrogen a solution of the compounds 25a and 25b (130 mg, 0.5 mmol) of Example 25 in dry THF (20 mL). The mixture was refluxed for 24 h and then cooled to 0° C., Aq. satd. NH$_4$Cl (20 mL) solution was added to destroy excess Grignard reagent and the solution was extracted with ethyl acetate (3×50 mL). The combined organic layers were dried over Na$_2$SO$_4$ and the solvent was evaporated to give an oil which was purified by chromatography (silica gel, 30% EtOAc in hexane) to give products 26a and 26b (130 mg, 94%). Separation of the products by HPLC [silica gel, EtOAC/hexane/ClCH$_2$CH$_2$Cl (3:7:10), 3 mL/min] gave 26a (25 mg, 18%) and 26b (95 mg, 69%) mp 78°-79° C. from hexane.

Compound 26a was obtained as a colorless oil. IR (film, NaCl): 3408, 2918, 1702, 1450, 1357, 1190, 1061 cm$^{-1}$. $^1$H NMR (CDCl$_3$): δ3.64 (t, J=6.7 Hz, 2H, HOCH$_2$), 2.80 (dd, J=5.7 Hz, J=2.5 Hz, 1H, CHCOCH$_3$), 2.12 (s, 3H, COCH$_3$), 0.93 (s, 3H, CH$_3$). $^{13}$C NMR (CDCl$_3$): δ212.96, (C=O), 61.7 (HOCH$_2$), 49.30 (C$^3$), 21.06 (CH$_3$). Elemental Analysis: For C$_{18}$H$_{30}$O$_2$. Calcd: C, 77.65; H, 10.86. Found: C, 77.72; H, 10.69. Structure:

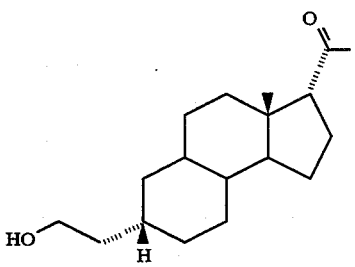

Compound 26b was obtained as white crystals: mp 78°-79° C. (from hexane). IR (film, NaCl): 3410, 2918, 1704, 1450, 1358, 1191, 1061 cm$^{-1}$. $^1$H NMR (CDCl$_3$): δ3.66 (t, J=6.9 Hz, 2H, HOCH$_2$), 2.55 (t, J=9.0 Hz, 1H, CHCO), 2.12 (s, 3H, COCH$_3$), 0.63 (s, 3H, CH$_3$). $^{13}$C NMR (CDCl$_3$): δ209.81 (C=O), 61.72 (HOCH$_2$), 55.65 (C$^3$), 13.53 (CH$_3$). Elemental Analysis: For C$_{18}$H$_{30}$O$_2$. Calcd: C, 77.65; H, 10.86. Found: C, 77.80; H, 10.88. Structure:

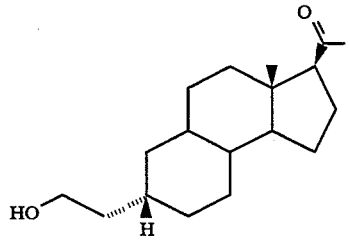

EXAMPLE 27

PREPARATION OF

[3S-(3α,3aα,5aβ,7Z,9aα,9bβ)]-7-(Carboethoxymethylene)dodecahydro-3a-methyl-1H-benz[e]inden-3-ol acetate (27Z) and

[3S-(3α,3aα,5aβ,7E,9aα,9bβ)]-7-(Carboethoxymethylene)dodecahydro-3a-methyl-1H-benz[e]inden-3-ol acetate (27E)

A stirred mixture of [3S-(3α,3aα,5aβ,9aα,9bβ)]-3-Acethyloxydodecahydro-3a-methyl-7H-benz[e]inden-7-one (3.49 g, 13.2 mmol) and (carbethoxymethylene)triphenylphosphorane (9.20 g, 26.4 mmol) under nitrogen was heated to 160° C. overnight (ca 16 h). The resultant brown colored liquid was cooled to room temperature and EtOAc (150 mL) was added. The solution was washed with water (180 mL) and brine (180 mL) and dried over Na$_2$SO$_4$. The organic layer was evaporated under reduced pressure to yield a gum which was purified by chromatography (silica gel, 10% EtOAc in hexane) to give products 27Z and 27E (4.12 g, 93%) as an oil. Separation of the products by HPLC (silica gel, 3% EtOAc in hexane, 3 mL/min) yielded product 27Z (first fraction) and product 27E (second fraction).

Compound 27Z was obtained as a colorless oil. IR (film, NaCl): 2924, 2871, 1738, 1714, 1648, 1448, 1377, 1246, 1147, 1092, 1045, 854 cm$^{-1}$. $^1$H NMR (CDCl$_3$): δ5.59 (s, 1H, CH=), 4.61 (t, J=8.4 Hz, 1H, CHOAc), 4.14 (q, J=7.1 Hz, 2H, OCH$_2$CH$_3$), 2.04 (s, 3H, CH$_3$COO), 1.27 (t, J=7.1 Hz, 3H, OCH$_2$CH$_3$), 0.84 (s, 3H, CH$_3$). $^{13}$C NMR (CDCl$_3$): δ171.18 (OC=O), 166.84 (OC=O), 162.31 (C=), 113.15 (C=), 82.51 (C$^3$), 59.48 (OCH$_2$CH$_3$), 21.14 (CH$_3$COO), 12.15 (CH$_3$). Elemental Analysis: For C$_{20}$H$_{30}$O$_4$. Calcd: C, 71.82; H, 9.04. Found: C, 71.71; H, 9.21. Structure:

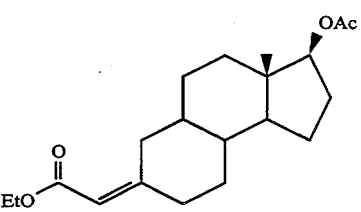

Compound 27E was obtained as a colorless oil. IR (film, NaCl): 2927, 2859, 1737, 1714, 1646, 1448, 1376, 1244, 1153, 1093, 1044, 865 cm$^{-1}$. $^1$H NMR (CDCl$_3$): δ5.60 (s, 1H, CH=), 4.60 (t, J=8.4 Hz, 1H, CHOAc), 4.14 (q, J=7.1 Hz, 2H, OCH$_2$CH$_3$), 2.04 (s, 3H, CH₃COO), 1.27 (t, J=7.2 Hz, 3H, OCH₂CH₃), 0.85 (s, 3H, CH₃). ¹³C NMR (CDCl₃): δ171.18 (OC=O), 166.80 (OC=O), 162.91 (C=), 113.15 (C=), 82.57 (C³), 59.44 (OCH₂CH₃), 21.16 (CH₃COO), 12.16 (CH₃). Elemental Analysis: For C₂₀H₃₀O₄. Calcd: C, 71.82; H, 9.04. Found: C, 72.00; H, 8.91. Structure:

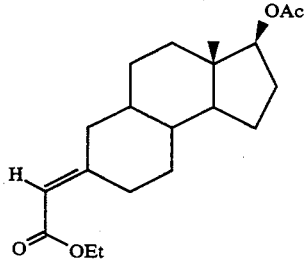

EXAMPLE 28

PREPARATION OF

[3S-(3α,3aα,5aβ,7Z,9aα,9bβ)]-Dodecahydro-7-(2-hydroxyethylidene)-3a-methyl-1H-benz[e]inden-3-ol (28Z) and

[3S-(3α,3aα,5aβ,7E,9aα,9bβ)]-Dodecahydro-7-(2-hydroxyethylidene)-3a-methyl-1H-benz[e]inden-3-ol (28E)

To a stirred solution of the mixture of compounds 27Z and 27E (3.97 g, 11.87 mmol) of Example 27 in dry dichloromethane (20 mL) was added diisobutylaluminium hydrid (1.0M solution in hexane, 142.4 mL, 142.4 mmol) at 0° C. After 4 h, dichloromethane/methanol (1:1, v/v, 40 mL) was added. Then, aq. 10% NaOH (150 mL) was added and the solution was extracted with dichloromethane (2×200 mL). The organic layer was washed with brine (2×100 mL) and water (200 mL) and dried over Na₂SO₄. After filtration, the solvent was removed to give a solid which was a mixture of 28Z and 28E (2.63 g, 89%). Compounds 28Z and 28E could not be separated directly. As described in Example 29, compounds 28Z and 28E were converted into compounds 29Z and 29E and then separated by HPLC. Samples of pure 28Z and 28E were obtained by hydrolysis (0.18% K₂CO₃ in aq. 70% CH₃OH for 2 h at room temperature) of separated compounds 29Z and 29E.

Compound 28Z was obtained as white crystals: mp 189°-190° C. (from CH₃OH/EtOAc). IR (KBr): 3311, 2949, 2915, 1667, 1469, 1443, 1350, 1245, 1133, 1086, 1059, 1022, 997, 859 cm⁻¹. ¹H NMR (DMSO): δ5.17 (t, J=6.5 Hz, 1H, CH=), 3.90 (t, J=5.8 Hz, 2H, HOCH₂), 3.46-3.34 (m, 1H, CHOH), 0.65 (s, 3H, CH₃). ¹³C NMR (DMSO): δ139.54 (C=), 122.56 (C=), 79.97 (C³), 56.76 (HOCH₂), 11.38 (CH₃). Elemental Analysis: For C₁₆H₂₆O₂. Calcd: C, 76.75; H, 10.47. Found: C, 76.45; H, 10.22. Structure:

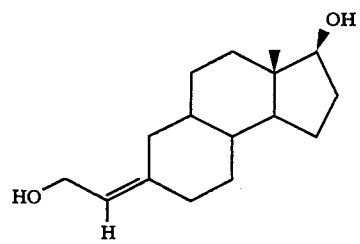

Compound 28E isomer was obtained as white crystals: mp 218°-219° C. (from EtOH/EtOAc). IR (KBr): 3280, 2928, 2901, 1668, 1468, 1444, 1351, 1240, 1134, 1091, 1057, 1016, 944, 858 cm⁻¹. ¹H NMR (DMSO): δ5.17 (t, J=6.5 Hz, 1H, CH=), 3.89 (t, J=5.9 Hz, 2H, HOCH₂), 3.46-3.33 (m, 1H, CHOH), 0.66 (s, 3H, CH₃). ¹³C NMR (DMSO): δ139.57 (C=), 122.42 (C=), 79.95 (C³), 56.73 (HOCH₂), 11.37 (CH₃). Elemental Analysis: For C₁₆H₂₆O₂. Calcd: C, 76.75; H, 10.47. Found: C, 76.60; H, 10.33. Structure:

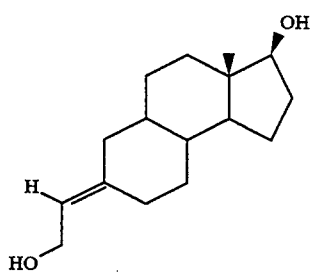

EXAMPLE 29

PREPARATION OF

[3S-(3α,3aα,5aβ,7Z,9aα,9bβ)]-7-(2-Acetyloxyethylidene)dodecahydro-3a-methyl-1H-benz[e]inden-3-ol (29Z) and

[3S-(3α,3aα,5aβ,7E,9aα,9bβ)]-7-(2-Acetyloxyethylidene)dodecahydro-3a-methyl-1H-benz[e]inden-3-ol (29E)

To a stirred solution of the mixture of compounds 28Z and 28E (1.20 g, 4.79 mmol) of Example 28 in dried collidine (30 mL) was added acetyl chloride (0.41 mL, 5.75 mmol) at a temperature of −40° C. The mixture was kept for 4 h at −40° C. and then for 2 h at 20° C. Dichloromethane (200 mL) and water (100 mL) were added, the heterogeneous mixture was cooled in an ice-water bath, and the aqueous phase was acidified with 3M HCl to pH=2. The organic layer was separated and the aqueous layer was extracted with dichloromethane (2×200 mL). The combined organic layers were washed with 5% NaHCO₃ (200 mL) and brine (200 mL) and dried over Na₂SO₄. The organic solvent was removed under reduced pressure to give products 29Z and 29E as an oil (1.15 g, 82%) which was separated by HPLC (silica gel, 20% EtOAc in hexane, 3 mL/min) into products 29Z (first fraction) and 29E (second fraction).

Compound 29Z was obtained as an oil. IR (film, NaCl): 3444, 2917, 2868, 1739, 1670, 1446, 1371, 1235, 1135, 1057, 1023, 955 cm⁻¹. ¹H NMR (CDCl₃): δ5.28 (t, J=6.8 Hz, 1H, CH=), 4.60-4.56 (m, 2H, AcOCH₂), 3.65 (t, J=8.5 Hz, 1H, CHOH), 2.05 (s, 3H, CH₃COO), 0.78 (s, 3H, CH₃). ¹³C NMR (CDCl₃): δ171.06

(OC=O), 146.14 (C=), 115.41 (C=), 81.70 (C³), 60.66 (AcOCH₂), 21.03 (CH₃COO), 11.13 (CH₃). Elemental Analysis: For C₁₈H₂₈O₃. Calcd: C, 73.93; H, 9.65. Found C, 73.81; H, 9.56. Structure:

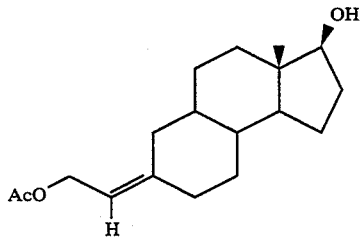

Compound 29E was obtained as a colorless oil. IR (film, NaCl): 3460, 2922, 2866, 1739, 1670, 1446, 1370, 1235, 1135, 1055, 1022, 954 cm⁻¹. ¹H NMR (CDCl₃): δ5.27 (t, J=6.8 Hz, 1H, CH=), 4.56 (d, J=7.1 Hz, 2H, AcOCH₂), 3.63 (t, J=8.5 Hz, 1H, CHOH), 2.04 (s, 3H, CH₃COO), 0.77 (s, 3H, CH₃). ¹³C NMR (CDCl₃): δ171.15 (C=O), 146.05 (C=), 115.22 (C=), 81.68 (C³), 60.71 (AcOCH₂), 21.04 (CH₃COO), 11.14 (CH₃). Elemental Analysis: For C₁₈H₂₈O₃. Calcd: C, 73.93; H, 9.65. Found: C, 73.77; H, 9.81. Structure:

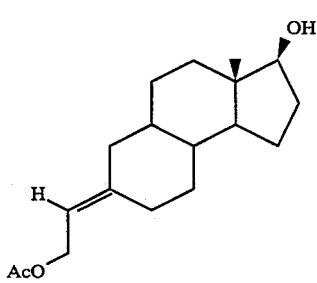

EXAMPLE 30

PREPARATION OF

[3aS-(3aα,5aβ,7Z,9aα,9bβ)]-7-(2-Acetyloxyethylidene)dodecahydro-3a-methyl-3H-benz[e]inden-3-one (30Z) and

[3aS-(3aα,5aβ,7E,9aα,9bβ)]-7-(2-Acetyloxyethylidene)dodecahydro-3a-methyl-3H-benz[e]inden-3-one (30E)

To a stirred solution of a mixture of compounds 29Z and 29E (1.15 g, 3.92 mmol) of Example 29 in acetone (100 mL) at 5° C. was added Jones reagent (8N, 1.3 mL). After 10 min, isopropanol (1 mL) was added to destroy excess Jones reagent, and EtOAc (200 mL) and water (200 mL) were added. The layers were separated and the aqueous layer was extracted with EtOAc (3×150 mL). The combined organic layers were washed with brine (3×150 mL) and dried over Na₂SO₄. After filtration, the solvent was removed under reduced pressure to give an oil which was a mixture of products 30Z and 30E (1.11 g, 97%) Compounds 30Z and 30E were separated by HPLC (silica gel, 10% EtOAc in hexane, 3 mL/min) to give products 30Z (first fraction) and 30E (second fraction).

Compound 30Z was obtained as an oil. IR (film, NaCl): 2927, 1740, 1670, 1452, 1370, 1024, 953 cm⁻¹. ¹H NMR (CDCl₃): δ5.32 (t, J=7.3 Hz, 1H, CH=), 4.58 (d, J=7.1 Hz, 2H, AcOCH₂), 2.06 (s, 3H, CH₃COO), 0.92 (s, 3H, CH₃). ¹³C NMR (CDCl₃): δ220.87 (C=O), 171.06 (OC=O), 145.32 (C=), 115.79 (C=), 60.59 (AcOCH₂), 21.06 (CH₃COO), 13.87 (CH₃). Elemental Analysis: For C₁₈H₂₆O₃. Calcd: C, 74.43; H, 9.05. Found: C, 74.26; H, 9.05. Structure:

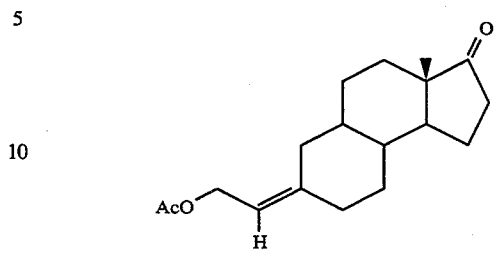

Compound 30E was obtained as an oil. IR (film, NaCl): 2924, 1739, 1670, 1450, 1371, 1233, 1171, 1025, 955 cm⁻¹. ¹H NMR (CDCl₃): δ5.31 (t, J=7.4 Hz, 1H, CH=), 4.63-4.55 (m, 2H, AcOCH₂), 2.06 (s, 3H, CH₃COO), 0.92 (s, 3H, CH₃). ¹³C NMR (CDCl₃): δ220.89 (C=O), 171.03 (OC=O), 145.4 (C=), 115.87 (C=), 60.57 (AcOCH₂), 21.04 (CH₃COO), 13.85 (CH₃). Elemental Analysis: For C₁₈H₂₆O₃. Calcd: C, 74.43; H, 9.05. Found: C, 74.21; H, 9.02. Structure:

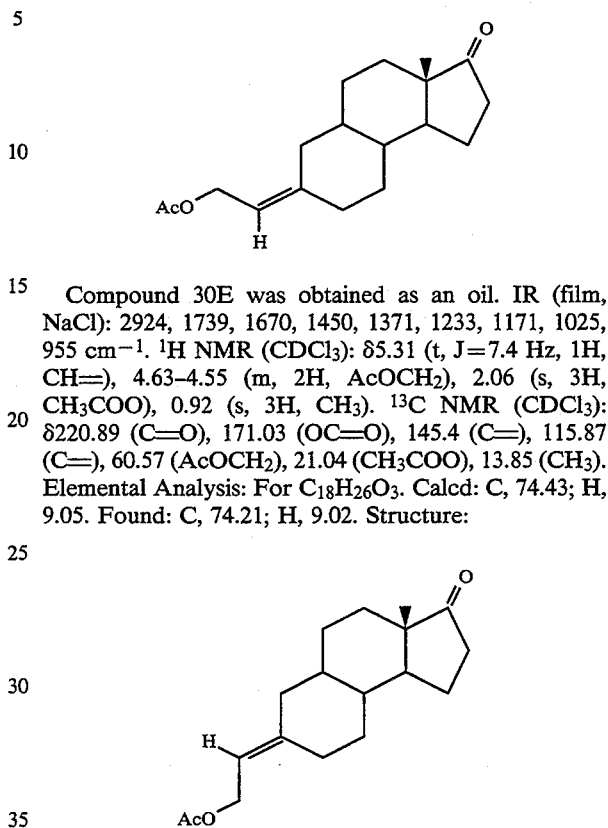

EXAMPLE 31

PREPARATION OF

[3aS-(3aα,5aβ,7Z,9aα,9bβ)]-Dodecahydro-7-(2-hydroxyethylidene)-3a-methyl-3H-benz[e]inden-3-one (31Z) and

[3aS-(3aα,5aβ,7E,9aα,9bβ)]-Dodecahydro-7-(2-hydroxyethylidene)-3a-methyl-3H-benz[e]inden-3-one (31E)

A mixture of compounds 30Z and 30E (200 mg, 0.69 mmol) of Example 30 was stirred for 2 h at ambient temperature in 0.18M aq. methanolic K₂CO₃(30 mL, 70% MeOH in water). After the addition of water (50 mL) and dichloromethane (100 mL), the aqueous layer was extracted with dichloromethane (2×100 mL). The combined organic layers were washed with brine (2×100 mL) and dried over Na₂SO₄. After filtration, the solvent was removed under reduced pressure to give an oil which was purified by chromatography (silica gel, 30% EtOAc in hexane) to yield products 31Z and 31E (170 mg, 99%) as an oil. Products 31Z and 31E were separated by HPLC (silica gel, 40% EtOAc in hexane, 3 mL/min) to give 31Z (first fraction) and 31E (second fraction).

Compound 31Z was obtained as white crystals: mp 98°-99° C. IR (film, NaCl): 3436, 2925, 1738, 1670, 1449, 1375, 1250, 1057, 1009, 825 cm⁻¹. ¹H NMR (CDCl₃): δ5.40 (t, J=7.1 Hz, 1H, CH=), 4.15 (d, J=7.0 Hz, 1H, HOCH₂), 0.92 (s, 3H, CH₃). ¹³C NMR (CDCl₃): δ221.04 (C=O), 142.80 (C=), 120.92 (C=), 58.42

(HOCH₂), 13.86 (CH₃). Elemental Analysis: For C₁₆H₂₄O₂. Calcd: C, 77.38; H, 9.74. Found: C, 77.50; H, 9.55. Structure:

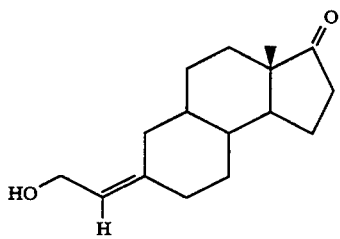

Compound 31E was obtained as a colorless oil. IR (film, NaCl): 3448, 2920, 1737, 1670, 1448, 1374, 1252, 1167, 1005, 892. cm⁻¹. ¹H NMR (CDCl₃): δ5.38 (t, J=7.1 Hz, 1H, CH═), 4.15 (d, J=7.1 Hz, 1H, HOCH₂), 0.92 (s, 3H, CH₃). ¹³C NMR (CDCl₃): δ221.07 (C═O), 142.70 (C═), 121.05 (C═), 58.38 (HOCH₂), 13.82 (CH₃). Elemental Analysis: For C₁₆H₂₄O₂. Calcd: C, 77.38; H, 9.74. Found C,77.27; H,9.53. Structure:

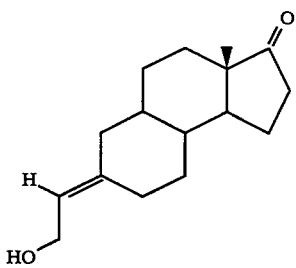

EXAMPLE 32

PREPARATION OF

[3R-(3α,3aβ,5aα,7Z,9aβ,9bα)]-Dodecahydro-7-(2-hydroxyethylidene)-3a-methyl-1H-benz[e]indene-3-carbonitrile (32a)

[3R-(3α,3aβ,5aα,7E,9aβ,9bα)]-Dodecahydro-7-(2-hydroxyethylidene)-3a-methyl-1H-benz[e]indene-3-carbonitrile (32b)

[3S-(3α,3aα,5aβ,7Z,9aα,9bβ)]-Dodecahydro-7-(2-hydroxyethylidene)-3a-methyl-1H-benz[e]indene-3-carbonitrile (32c)

[3S-(3α,3aα,5aβ,7E,9aα,9bβ)]-Dodecahydro-7-(2-hydroxyethylidene)-3a-methyl-1H-benz[e]indene-3-carbonitrile (32d)

A mixture of compounds 30Z and 30E (100 mg, 0.34 mmol) of Example 30 was stirred with diethyl phosphorocyanidate (154 μL, 1.02 mmol) and LiCN (33.6 mg, 1.02 mmol) in THF (10 mL) at room temperature for 10-30 min. Water (10 mL) was added and the mixture was then extracted with EtOAc (2×50 mL). The combined organic layers were washed with brine (2×50 mL) and dried over Na₂SO₄. After filtration, the solvent was removed under reduced pressure to give an oil which was purified by chromatography (silica gel, 40% EtOAc in hexane) to give the first intermediates (155 mg, 99%) as an oil.

To a solution of SMI₂ (1.02 mmol, 10.2 mL of 0.1M solution in THF) was added a solution of the first intermediates (154 mg, 0.34 mmol) and methanol (0.34 mmol, 14 μL) in THF (5 mL) at room temperature. This reaction mixture was stirred for 16 h, then aq. 10% HCl (10 mL) was added and the solution was extracted with EtOAc (2×100 mL). The combined organic layers were washed with brine (2×100 mL) and 5% Na₂S₂O₃ (10 mL) and brine (2×50 mL) and dried over Na₂SO₄. After filtration, the solvent was removed under reduced pressure to give an oil which was purified by chromatography (silica gel, 20% EtOAc in hexane) to give the second intermediates (70 mg, 68%) as an oil and products 32a-32d (27 mg, 31%) as an oil.

A similarly prepared quantity of the second intermediates (400 mg, 1.33 mmol) was stirred for 2 h at ambient temperature in 0.18M aq. methanolic K₂CO₃ (80 mL, 70% MeOH in water). After the addition of water (200 mL) and dichloromethane (200 mL), the separated aqueous layer was extracted with dichloromethane (2×200 mL). The combined organic layers were washed with brine (2×200 mL) and dried over Na₂SO₄. After filtration, the solvent was removed under reduced pressure to give an oil which was purified by chromatography (silica gel, 30% EtOAc in hexane) to yield products 32a-32d (320 mg, 93%) as an oil. Products 32a-32d were separated by HPLC (silica gel, 30% EtOAc in hexane, 3 mL/min) into a mixture of products 32a-32b and products 32c-32d. Each pair of products was separated by HPLC (silica gel, 20% ETOAc in hexane/3 mL/min) to give separated products 32a-32d.

Compound 32a was obtained as white crystals: mp 74°-75° C. IR (film, NaCl): 3394, 2926, 2862, 2234, 1669, 1449, 1385, 1084, 1007, 918, 892 cm⁻¹. ¹H NMR (CDCl₃): δ5.39 (t, J=7.1 Hz, 1H, CH═), 4.15 (d, J=7.2 Hz, 1H, HOCH₂), 2.60-2.57 (m, 2H, CHCN & ring H), 0.86 (s, 3H, CH₃). ¹³C NMR (CDCl₃): δ142.77 (C═), 120.81 (C═), 122.12 (CN), 58.40 (HOCH₂), 18.07 (CH₃). Elemental Analysis: For C₁₇H₂₅NO₂. Calcd: C, 78.72; H, 9.71, N, 5.40. Found: C, 78.72; H, 9.77, N, 5.37. Structure:

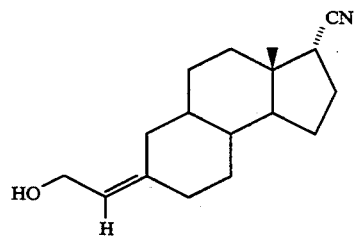

Compound 32b was obtained as white crystals: mp 111°-112° C. IR (film, NaCl): 3405, 2921, 2865, 2234, 1670, 1448, 1384, 1007 cm⁻¹. ¹H NMR (CDCl₃): δ5.38 (t, J=7.1 Hz, 1H, CH═), 4.15 (d, J=7.1 Hz, 2H, HOCH₂), 2.58 (dd, J=6.9 Hz, J=2.0 Hz, 1H, CHCN), 0.86 (s, 3H, CH₃). ¹³C NMR (CDCl₃): δ142.97 (C═), 120.96 (C═), 122.19 (CN), 58.55 (HOCH₂), 18.13 (CH₃). Elemental Analysis: For C₁₇H₂₅NO₂. Calcd. C, 78.72; H, 9.71, N, 5.40. Found: C, 78.51; H, 9.62, N, 5.39. Structure:

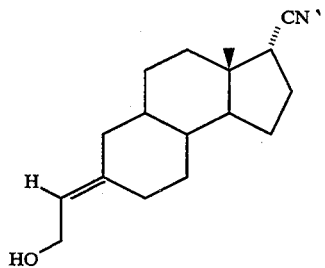

Compound 32c was obtained as white crystals: mp 115°–116° C. IR (film, NaCl): 3368, 2922, 2236, 1668, 1448, 1387, 1084, 1005 cm$^{-1}$. $^1$H NMR (CDCl$_3$): δ5.38 (t, J=7.1 Hz, 1H, CH=), 4.14 (d, J=7.1 Hz, 1H, HOCH$_2$), 2.30 (t, J=6.8 Hz, CHCN), 0.97 (s, 3H, CH$_3$). $^{13}$C NMR (CDCl$_3$); δ143.04 (C=), 120.78 (C=), 121.27 (CN), 58.52 (HOCH$_2$), 14.42 (CH$_3$). Elemental Analysis: For C$_{17}$H$_{25}$NO$_2$. Calcd: C, 78.72; H, 9.71, N, 5.40. Found: C, 78.67; H, 9.71. N, 5.39. Structure:

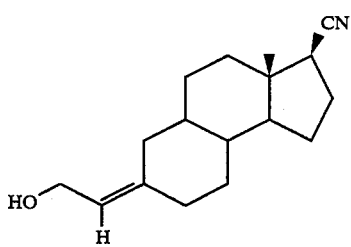

Compound 32d was obtained as white crystal: mp 93°–94° C. IR (film, NaCl): 3458, 2919, 2236, 1670, 1448, 1387, 1003 cm$^{-1}$. $^1$H NMR (CDCl$_3$): δ5.38 (t, J=7.1 Hz, 1H, CH=), 4.14 (d, J=7.2 Hz, 1H, HOCH$_2$), 2.30 (t, J=9.5 Hz, 1H, CHCN), 0.96 (s, 3H, CH$_3$). $^{13}$C NMR (CDCl$_3$): δ143.05 (C=), 120.95 (C=), 121.27 (CN), 58.55 (HOCH$_2$), 14.42 (CH$_3$). Elemental Analysis: For C$_{17}$H$_{25}$NO$_2$. Calcd: C, 78.72; H, 9.71, N, 5.40. Found: C, 78.61; H, 9.53, N, 5.15. Structure:

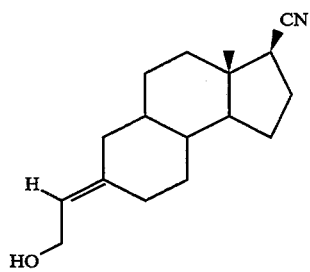

Various other examples will be apparent to the person skilled in the art after reading the present disclosure without departing from the spirit and scope of the invention. It is intended that all such other examples be included within the scope of the appended claims.

What is claimed is:

1. A compound of the formula

2. A compound selected from the group consisting of

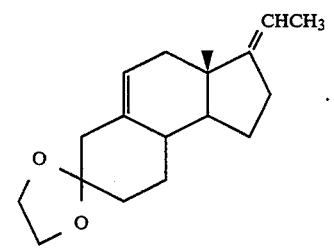

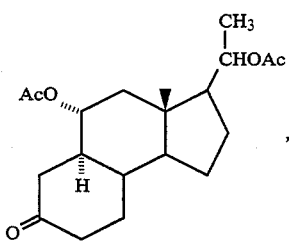

,

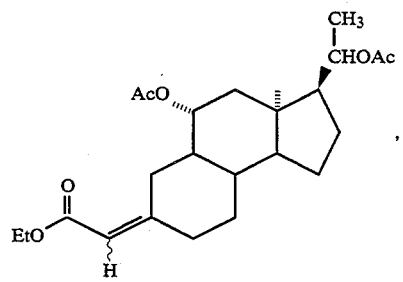

,

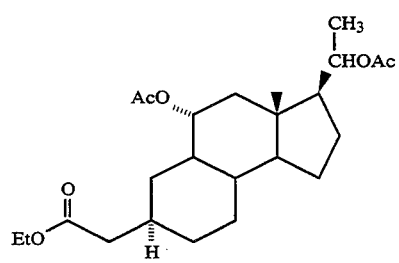

and

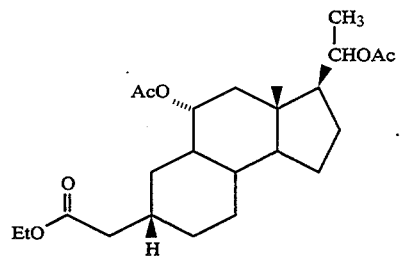

3. A compound selected from the group consisting of

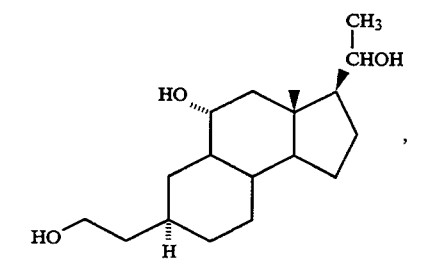
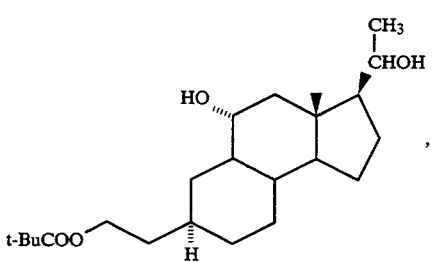
and
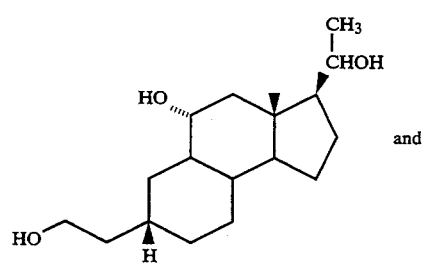
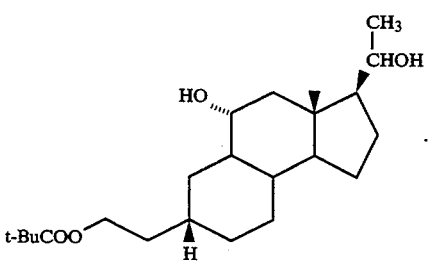
4. A compound selected from the group consisting of
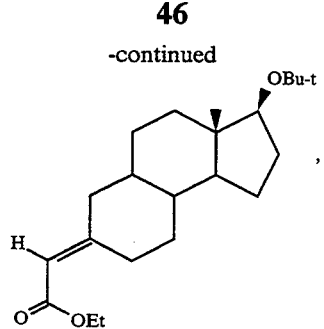
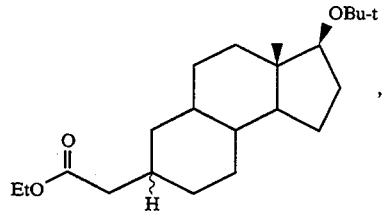
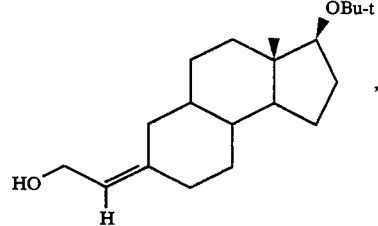
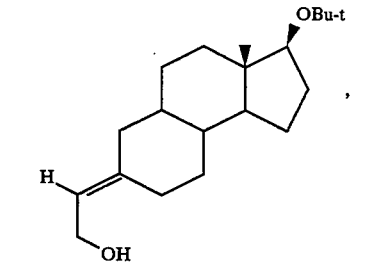
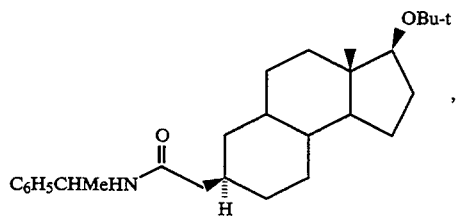
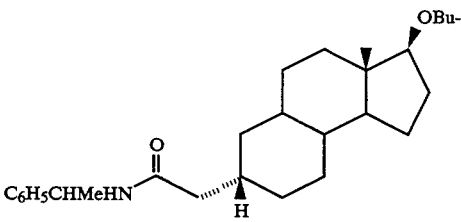
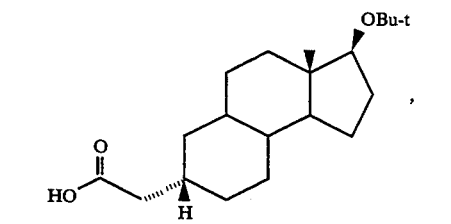

-continued
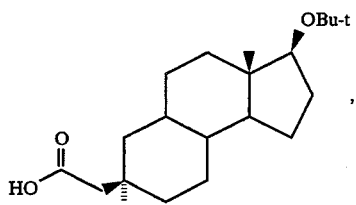,
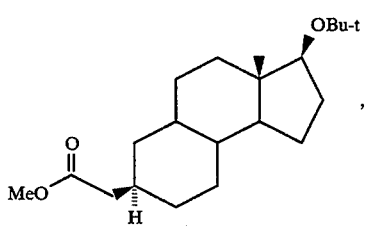,
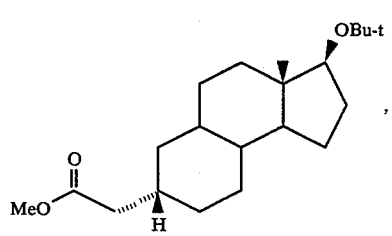,
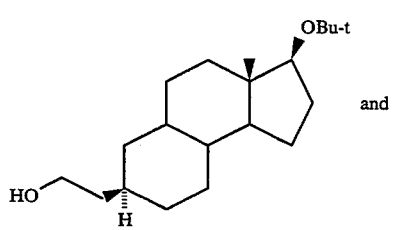 and
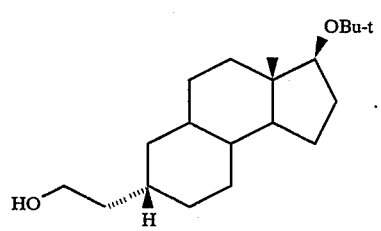
5. A compound selected from the group consisting of
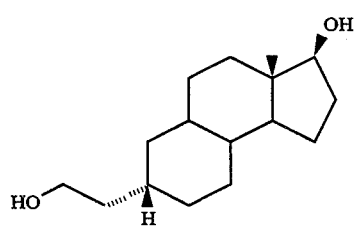
and
-continued
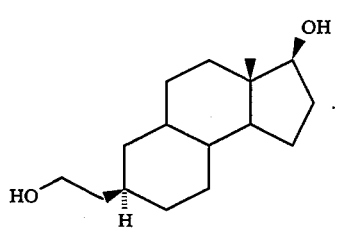
6. A compound selected from the group consisting of
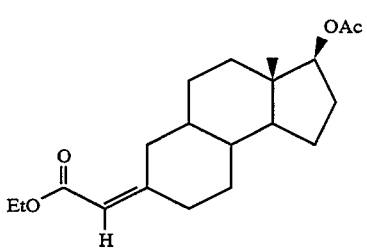
and
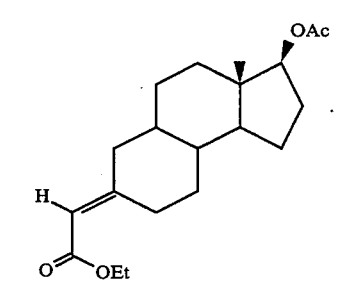
7. A compound selected from the group consisting of
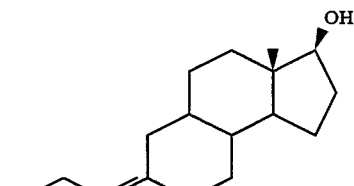,
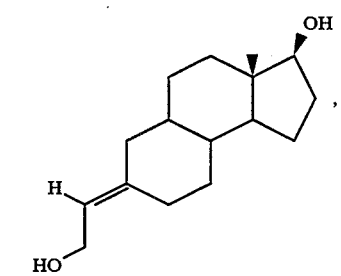, -continued

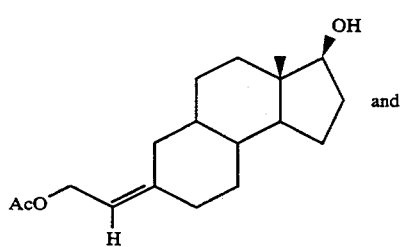 and

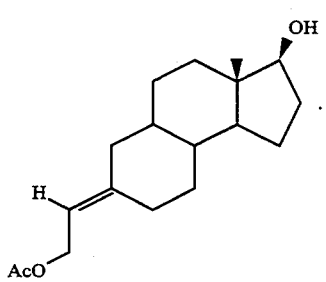

8. A compound selected from the group consisting of

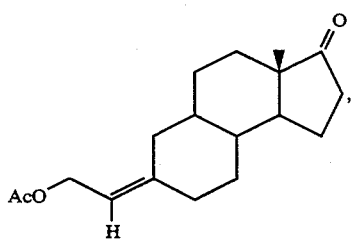

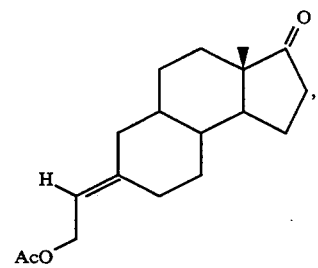 and

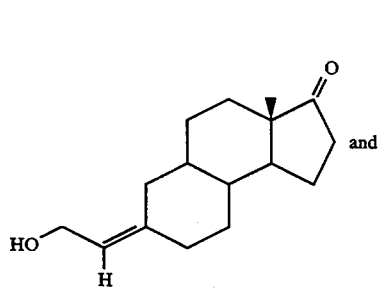

-continued

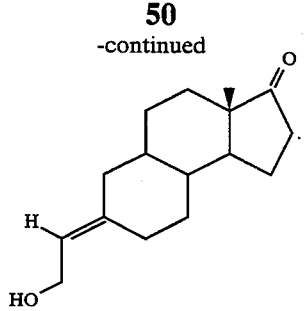

9. A compound selected from the group consisting of

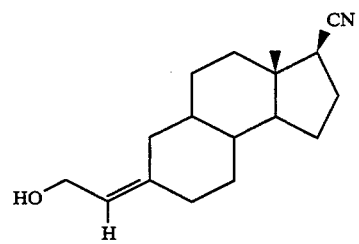

and

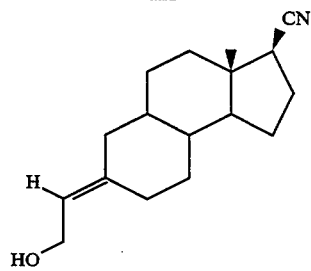

10. A process for the synthesis of

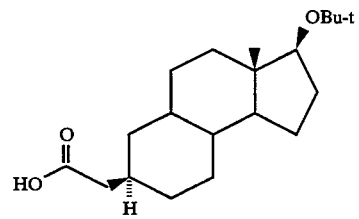

or

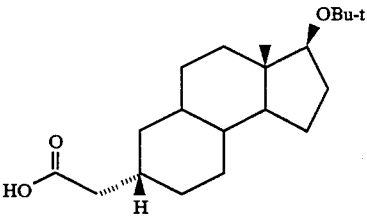

which comprises reacting

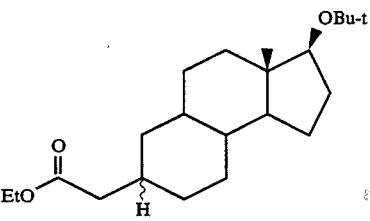

with optically active phenylethylamine, separating the resulting 5α and 5β series of amides by silica gel chromatography, acidifying the separated 5α or 5β amide and retaining the resulting 5α acid or 5β acid as the desired product.

* * * * *